United States Patent
Stormont et al.

(10) Patent No.: US 11,567,153 B2
(45) Date of Patent: Jan. 31, 2023

(54) SYSTEMS FOR A RADIO FREQUENCY COIL FOR MR IMAGING

(71) Applicant: General Electric Company, Schenectady, NY (US)

(72) Inventors: Robert Steven Stormont, Waukesha, WI (US); Scott Allen Lindsay, Waukesha, WI (US); Dashen Chu, Waukesha, WI (US); Ricardo M. Matias, Stevenson Ranch, CA (US)

(73) Assignee: General Electric Company, Schenectady, NY (US)

( * ) Notice: Subject to any disclaimer, the term of this patent is extended or adjusted under 35 U.S.C. 154(b) by 848 days.

(21) Appl. No.: 16/463,393

(22) PCT Filed: Nov. 22, 2017

(86) PCT No.: PCT/US2017/062983
§ 371 (c)(1),
(2) Date: May 23, 2019

(87) PCT Pub. No.: WO2018/098255
PCT Pub. Date: May 31, 2018

(65) Prior Publication Data
US 2019/0353722 A1 Nov. 21, 2019

Related U.S. Application Data

(60) Provisional application No. 62/425,975, filed on Nov. 23, 2016.

(51) Int. Cl.
*G01R 33/3415* (2006.01)
*G01R 33/36* (2006.01)
(Continued)

(52) U.S. Cl.
CPC ........ *G01R 33/3415* (2013.01); *A61B 5/6803* (2013.01); *G01R 33/3628* (2013.01);
(Continued)

(58) Field of Classification Search
CPC ............ G01R 33/3415; G01R 33/3628; G01R 33/3685; G01R 33/34084; G01R 33/3657;
(Continued)

(56) References Cited

U.S. PATENT DOCUMENTS 4,621,237 A 11/1986 Timms
4,825,162 A 4/1989 Roemer
(Continued)

FOREIGN PATENT DOCUMENTS

CN 1969191 A 5/2007
CN 103064045 B 4/2017
(Continued)

OTHER PUBLICATIONS

European application No. 17874224.3 filed Nov. 22, 2017—European extended Search Report dated Oct. 30, 2020; 12 pages.
(Continued)

*Primary Examiner* — Rishi R Patel

(57) ABSTRACT

Various methods and systems are provided for a flexible, lightweight and low-cost stretchable radio frequency (RF) coil of a magnetic resonance imaging (MRI) system. In one example, a RF coil assembly for a MRI system includes a loop portion comprising distributed capacitance conductor wires, a coupling electronics portion including a pre-amplifier; and a stretchable material to which the loop portion and coupling electronics portion are attached and/or enclosed therein.

20 Claims, 13 Drawing Sheets

(51) Int. Cl.
*A61B 5/00* (2006.01)
*A61B 5/055* (2006.01)
*G01R 33/34* (2006.01)

(52) U.S. Cl.
CPC ........ *G01R 33/3685* (2013.01); *A61B 5/0042* (2013.01); *A61B 5/055* (2013.01); *G01R 33/34084* (2013.01); *G01R 33/3657* (2013.01)

(58) Field of Classification Search
CPC ............ G01R 33/34007; A61B 5/6803; A61B 5/0042; A61B 5/055
See application file for complete search history.

(56) References Cited

U.S. PATENT DOCUMENTS

| | | | |
|---|---|---|---|
| 5,435,302 | A | 7/1995 | Lenkinski |
| 5,682,098 | A | 10/1997 | Vij |
| 5,905,378 | A | 5/1999 | Giaquinto |
| 6,084,411 | A | 7/2000 | Giaquinto |
| 6,501,980 | B1 | 12/2002 | Carlon |
| 6,650,926 | B1 | 11/2003 | Chan |
| 6,836,117 | B2 | 12/2004 | Mitsuru |
| 6,980,000 | B2 | 12/2005 | Wong |
| 7,177,671 | B2 | 2/2007 | Nabetani |
| 7,212,002 | B2 | 5/2007 | Helmut |
| 7,450,984 | B2 | 11/2008 | Engelhard |
| 7,619,416 | B2 | 11/2009 | Nordmeyer-Massner |
| 7,945,308 | B2 | 5/2011 | Tropp |
| 8,046,046 | B2 | 10/2011 | Chan |
| 8,179,136 | B2 | 5/2012 | Chan |
| 8,207,736 | B2 | 6/2012 | Chu |
| 8,269,498 | B2 | 9/2012 | Zhang |
| 8,362,776 | B2 | 1/2013 | Chu |
| 8,441,258 | B2 | 5/2013 | Chan |
| 8,487,620 | B2 | 7/2013 | Brown |
| 8,598,880 | B2 | 12/2013 | Dalveren |
| 8,624,597 | B2 | 1/2014 | Banerjee |
| 9,000,766 | B2 | 4/2015 | Chu |
| 9,002,431 | B2 | 4/2015 | Jones |
| 9,678,180 | B2 | 6/2017 | Yang |
| 10,983,185 | B2 * | 4/2021 | Stack ................. G01R 33/3685 |
| 11,280,859 | B2 * | 3/2022 | Dalveren .......... G01R 33/34046 |
| 2005/0007116 | A1 | 1/2005 | Davis |
| 2007/0279061 | A1 * | 12/2007 | Erickson ............. G01R 33/5659 324/322 |
| 2008/0204021 | A1 | 8/2008 | Leussler |
| 2008/0284436 | A1 | 11/2008 | Weizenecker |
| 2012/0153955 | A1 | 6/2012 | Wong |
| 2013/0093425 | A1 * | 4/2013 | Chu ................ G01R 33/34084 336/200 |
| 2013/0137969 | A1 | 5/2013 | Jones |
| 2013/0184566 | A1 | 7/2013 | Kreischer |
| 2013/0320981 | A1 | 12/2013 | Bulumulla |
| 2014/0210466 | A1 | 7/2014 | Arias |
| 2015/0173678 | A1 | 6/2015 | Jones |
| 2015/0293192 | A1 * | 10/2015 | Schmidt ............... H01F 17/045 324/322 |

FOREIGN PATENT DOCUMENTS

| | | |
|---|---|---|
| EP | 2110680 A1 | 10/2009 |
| JP | 2003024294 A | 1/2003 |

OTHER PUBLICATIONS

Balthazar Lechene, et al.; High quality printed receive coils for clothing integration, PowerPoint presentation; ISMRM 24th Annual Meeting & Exhibition, May 7-13, 2016; Singapore; 20 pages.
Bei Zhang, et al.; High Impedance Detector Arrays for Magnetic Resonance; arXiv 1709.03416v1 [physics.ins-det] Sep. 11, 2017; 16 pages.
Joseph R. Corea, et al.; Screen-printed flexible MRI receive coils; Nature Communications, 7:10839, DOI:10.1038/ncomms10839, www.nature.com/naturecommunications; Mar. 10, 2016; 7 pages.
JP 2003-24294A English Abstract, obtained from Espacenet Nov. 17, 2021.
JP application 2019-527375 filed May 21, 2019—Office Action dated Aug. 31, 2021; Machine Translation Sep. 1, 2021; 5 pages.
Korean Office Action dated May 25, 2020, 7 pages.

\* cited by examiner

SYSTEMS FOR A RADIO FREQUENCY COIL FOR MR IMAGING

CROSS REFERENCE TO RELATED APPLICATIONS

The present application claims priority to U.S. Provisional Patent Application No. 62/425,975, entitled "SYSTEMS FOR A RADIO FREQUENCY COIL FOR MR IMAGING," filed Nov. 23, 2016, the entire contents of which are hereby incorporated by reference for all purposes.

FIELD

Embodiments of the subject matter disclosed herein relate to magnetic resonance imaging (MRI), and more particularly, to MRI radio frequency (RF) coils.

BACKGROUND

Magnetic resonance imaging (MRI) is a medical imaging modality that can create images of the inside of a human body without using x-rays or other ionizing radiation. MRI systems include a superconducting magnet to create a strong, uniform, static magnetic field. When a human body, or part of a human body, is placed in the magnetic field, the nuclear spins associated with the hydrogen nuclei in tissue water become polarized, wherein the magnetic moments associated with these spins become preferentially aligned along the direction of the magnetic field, resulting in a small net tissue magnetization along that axis. MRI systems also include gradient coils that produce smaller amplitude, spatially-varying magnetic fields with orthogonal axes to spatially encode the magnetic resonance (MR) signal by creating a signature resonance frequency at each location in the body. Radio frequency (RF) coils are then used to create pulses of RF energy at or near the resonance frequency of the hydrogen nuclei, which add energy to the nuclear spin system. As the nuclear spins relax back to their rest energy state, they release the absorbed energy in the form of a MR signal. This signal is detected by the MRI system and is transformed into an image using a computer and known reconstruction algorithms.

As mentioned, RF coils are used in MRI systems to transmit RF excitation signals ("transmit coil"), and to receive the MR signals emitted by an imaging subject ("receive coil"). Coil-interfacing cables may be used to transmit signals between the RF coils and other aspects of the processing system, for example to control the RF coils and/or to receive information from the RF coils. However, conventional RF coils tend to be bulky, rigid and are configured to be maintained at a fixed position relative to other RF coils in an array. This bulkiness and lack of flexibility often prevents the RF coil loops from coupling most efficiently with the desired anatomy and make them very uncomfortable to the imaging subject. Further, coil-to-coil interactions dictate that the coils be sized and/or positioned non-ideally from a coverage or imaging acceleration perspective.

BRIEF DESCRIPTION

In one embodiment, a radio frequency (RF) coil assembly for a magnetic resonance (MRI) system includes a loop portion comprising distributed capacitance wires, a coupling electronics portion including a pre-amplifier, and a stretchable material to which the loop portion and coupling electronics are attached or enclosed therein. In this way, a flexible and stretchable RF coil assembly may be provided that allows for RF coils in an array to be positioned more arbitrarily, allowing placement and/or size of the coils to be based on desired anatomy coverage, without having to account for fixed coil overlaps or electronics positioning. The coils may deform, overlap, and/or elongate, allowing the RF coils to be placed on or enclosed within stretchable material, which may allow the coils to adapt and conform around the patient anatomy and increase coverage of the anatomy by the coils. Further, a stretchable RF coil array as described herein may allow a single RF coil array to accommodate a variety of patient sizes. Additionally, the cost and weight of the coils may be significantly lowered due to minimized materials and production process, and environmentally-friendlier processes may be used in the manufacture and miniaturization of the RF coils of the present disclosure versus conventional coils.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
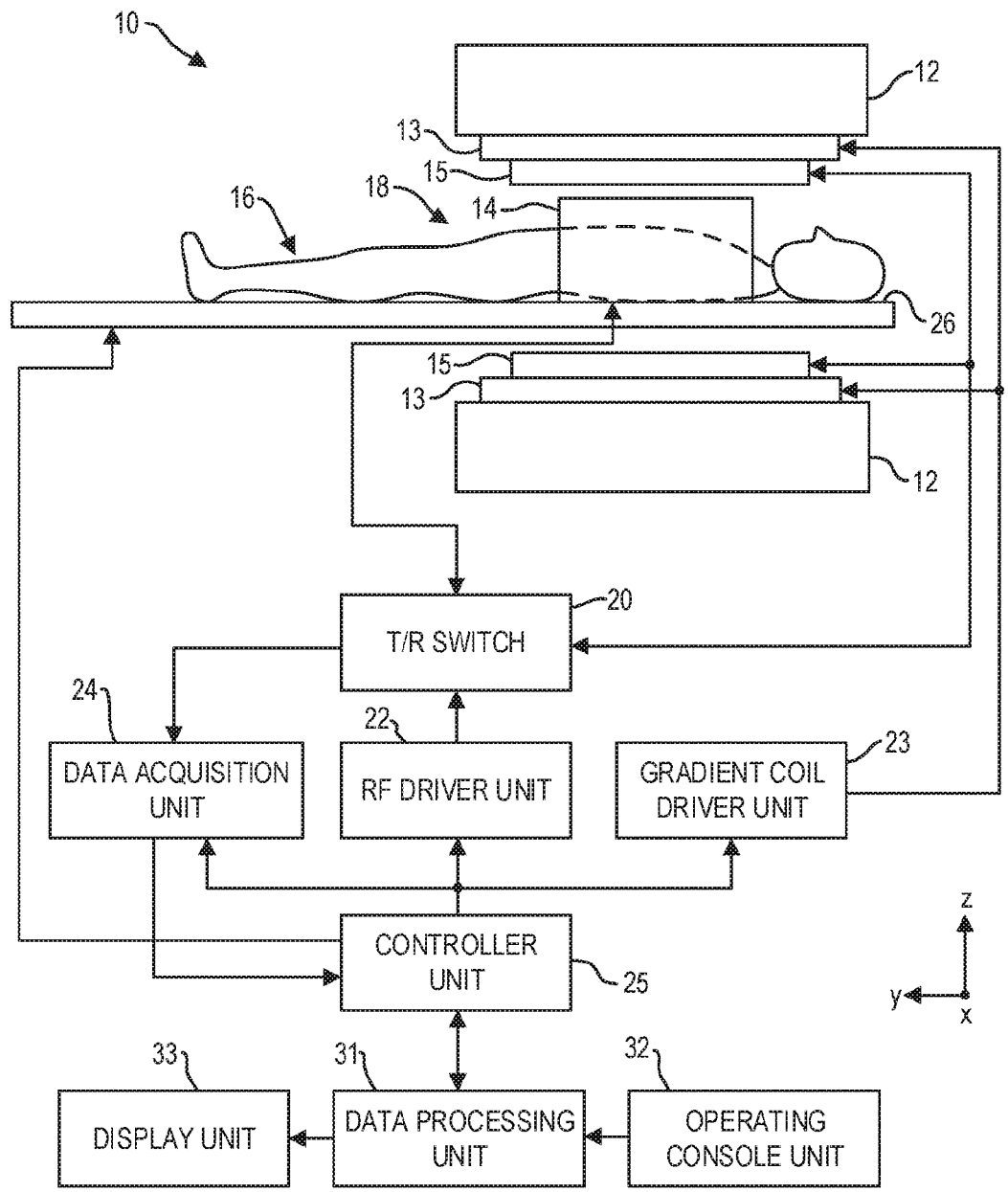
FIG. 1 is a block diagram of an MRI system according to an embodiment.

The following description relates to various embodiments of a radio frequency (RF) coil in MRI systems. In particular, systems and methods are provided for a low-cost, flexible, and lightweight RF coil that is effectively transparent in multiple respects. The RF coil is effectively transparent to patients, given the low weight of the coil and flexible packaging that is enabled by the RF coil. The RF coil is also effectively transparent to other RF coils in an array of RF coils, due to minimization of magnetic and electric coupling mechanisms, allowing the incorporation of the coils into a stretchable coil array. Further, the RF coil is effectively transparent to other structures through capacitance minimization and is transparent to positrons through mass reduction, enabling use of the RF coil in hybrid positron emission tomography (PET)/MR imaging systems. The RF coil of the present disclosure may be used in MRI systems of various magnetic field strengths.

The RF coil of the present disclosure includes a significantly smaller amount of copper, printed circuit board (PCB) material and electronic components than used in a conventional RF coil and includes parallel elongated wire conductors, encapsulated and separated by a dielectric material, forming the coil element. The parallel wires form a low reactance structure without need for discrete capacitors. The minimal conductor, sized to keep losses tolerable, eliminates much of the capacitance between coil loops, and reduces electric field coupling. By interfacing with a large sampling impedance, currents are reduced and magnetic field coupling is minimized. The electronics are minimized in size and content to keep mass and weight low and prevent excessive interaction with the desired fields. Packaging can now be extremely flexible and/or stretchable, which allows conforming to anatomy, optimizing signal to noise ratio (SNR) and imaging acceleration.

A traditional RF receive coil for MR is comprised of several conductive intervals joined between themselves by capacitors. By adjusting the capacitors' values, the impedance of the RF coil may be brought to its minimal value, usually characterized by low resistance. At resonant frequency, stored magnetic and electric energy alternate periodically. Each conductive interval, due to its length and width, possesses a certain self-capacitance, where electric energy is periodically stored as static electricity. The distribution of this electricity takes place over the entire conductive interval length of the order of 5-15 cm, causing similar range electric dipole field. In a proximity of a large dielectric load, self-capacitance of the intervals change—hence detuning of the coil. In case of a lossy dielectric, dipole electric field causes Joule dissipation characterized by an increase overall resistance observed by the coil.

In contrast, the RF coil of the present disclosure represents almost an ideal magnetic dipole antenna as its common mode current is uniform in phase and amplitude along its perimeter. The capacitance of the RF coil is built between the two wires along the perimeter of the loop. The conservative electric field is strictly confined within the small cross-section of the two parallel wires and dielectric filler material. In the case of two RF coil loops overlapping, the parasitic capacitance at the cross-overs is greatly reduced in comparison to two overlapped copper traces of traditional RF coils. RF coil thin cross-sections allows better magnetic decoupling and reduces or eliminates critical overlap between two loops in comparison to two traditional trace-based coil loops.

FIG. 1 illustrates a magnetic resonance imaging (MRI) apparatus 10 that includes a superconducting magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In one example, the RF coil unit 14 is a surface coil, which is a local coil that is typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are independent but electromagnetically coupled structures. The MRI apparatus 10 transmits electromagnetic pulse signals to the subject 16 placed in an imaging space 18 with a static magnetic field formed to perform a scan for obtaining magnetic resonance signals from the subject 16 to reconstruct an image of a slice of the subject 16 based on the magnetic resonance signals thus obtained by the scan.

The superconducting magnet unit 12 includes, for example, an annular superconducting magnet, which is mounted within a toroidal vacuum vessel. The magnet defines a cylindrical space surrounding the subject 16, and generates a constant, strong, uniform, static magnetic field along the Z direction of the cylindrical space.

The MRI apparatus 10 also includes the gradient coil unit 13 that generates a gradient magnetic field in the imaging space 18 so as to provide the magnetic resonance signals received by the RF coil unit 14 with three-dimensional positional information. The gradient coil unit 13 includes three gradient coil systems, each of which generates a gradient magnetic field, which inclines into one of three spatial axes perpendicular to each other, and generates a gradient magnetic field in each of frequency encoding direction, phase encoding direction, and slice selection direction in accordance with the imaging condition. More specifically, the gradient coil unit 13 applies a gradient field in the slice selection direction of the subject 16, to select the slice; and the RF body coil unit 15 transmits an RF signal to a selected slice of the subject 16 and excites it. The gradient coil unit 13 also applies a gradient field in the phase encoding direction of the subject 16 to phase encode the magnetic resonance signals from the slice excited by the RF signal. The gradient coil unit 13 then applies a gradient magnetic field in the frequency encoding direction of the subject 16 to frequency encode the magnetic resonance signals from the slice excited by the RF signal.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field is formed by the superconducting magnet unit 12, the RF coil unit 14 transmits, based on a control signal from the controller unit 25, an RF signal that is an electromagnet wave to the subject 16 and thereby generates a high-frequency magnetic field. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. The RF coil unit 14 may transmit and receive an RF signal using the same RF coil.

The RF body coil unit 15 is disposed, for example, to enclose the imaging space 18, and produces RF magnetic field pulses orthogonal to the main magnetic field produced by the superconducting magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as those comprising the RF coil unit 14 can transmit to or receive signals from only a localized region of the subject 16, the RF body coil unit 15 generally have a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode, a receive-only mode, or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coil unit 14 and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 14.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) of the subject 16 generated by the data processing unit 31.

During a scan, RF coil array interfacing cables (not shown) may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local surface RF coil unit 14 receives the MR signals. More generally, RF coils are used to transmit RF excitation signals ("transmit coil"), and to receive the MR signals emitted by an imaging subject ("receive coil"). In an example, the transmit and receive coils are a single mechanical and electrical structure or array of structures, with transmit/receive mode switchable by auxiliary circuitry. In other examples, the transmit body coil (e.g., RF body coil unit 15) and the surface receive coil (e.g., RF coil unit 14) may be independent structures that are physically coupled to each other via a data acquisition unit or other processing unit. For enhanced image quality, however, it may be desirable to provide a receive coil that is mechanically and electrically isolated from the transmit coil. In such case it is desirable that the receive coil, in its receive mode, be electromagnetically coupled to and resonant with an RF "echo" pulse that is stimulated by the transmit coil. However, during transmit mode, it may be desirable that the receive coil is electromagnetically decoupled from and therefore not resonant with the transmit coil, during actual transmission of the RF signal. Such decoupling averts a potential problem of noise produced within the auxiliary circuitry when the receive coil couples to the full power of the RF signal. Additional details regarding the uncoupling of the receive RF coil will be described below.

As mentioned previously, traditional RF coils may include acid etched copper traces (loops) on PCBs with lumped electronic components (e.g., capacitors, inductors, baluns, resistors, etc.), matching circuitry, decoupling circuitry, and pre-amplifiers. Such a configuration is typically very bulky, heavy, and rigid, and requires relatively strict placement of the coils relative to each other in an array to prevent coupling interactions among coil elements that may degrade image quality. As such, traditional RF coils and RF coil arrays lack flexibility and hence may not conform to patient anatomy, degrading imaging quality and patient comfort.

Thus, according to embodiments disclosed herein, an RF coil array, such as RF coil unit 14, may include distributed capacitance wires rather than copper traces on PCBs with lumped electronic components. As a result, the RF coil array may be lightweight and flexible, allowing placement in low-cost, lightweight, waterproof, and/or flame retardant fabrics or materials. The coupling electronics portion coupling the loop portion of the RF coil (e.g., the distributed capacitance wire) may be miniaturized and utilize a low input impedance pre-amplifier, which is optimized for high source impedance (e.g., due to impedance matching circuitry) and allows flexible overlaps among coil elements in an RF coil array. Further, the RF coil array interfacing cable between the RF coil array and system processing components may be flexible and include integrated transparency functionality in the form of distributed baluns, which allows rigid electronic components to be avoided and aids in spreading of the heat load.

Figure 2:
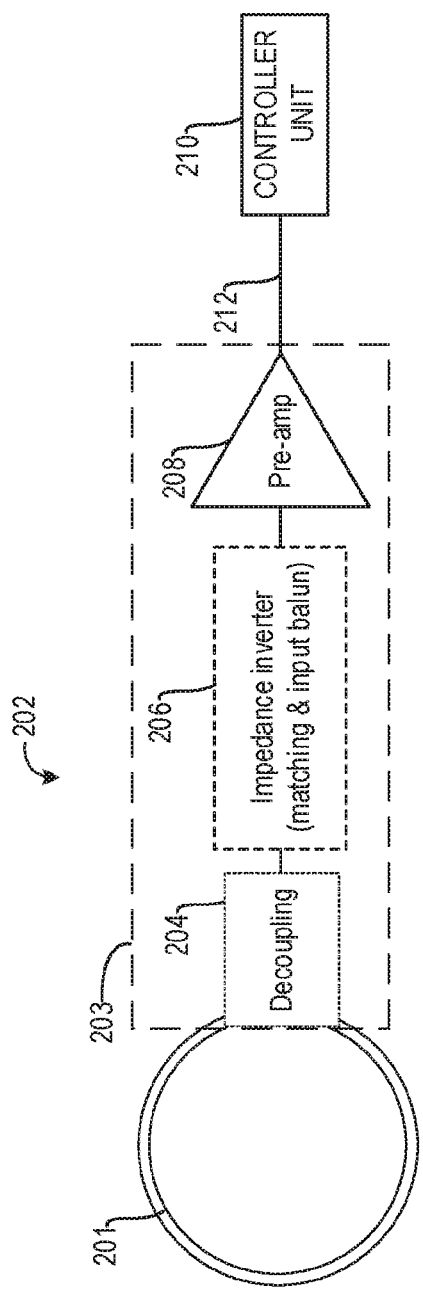
FIG. 2 schematically shows an example RF coil coupled to a controller unit.

Turning now to FIG. 2, a schematic view of an RF coil 202 including a loop portion 201 coupled to a controller unit 210 via coupling electronics portion 203 and a coil-interfacing cable 212 is shown. In one example, the RF coil may be a surface receive coil, which may be single- or multi-channel. The RF coil 202 is one non-limiting example of RF coil unit 14 of FIG. 1 and as such may operate at one or more frequencies in the MRI apparatus 10. The coil-interfacing cable 212 may be a coil-interfacing cable extending between the coupling electronics portion 203 and an interfacing connector of an RF coil array or a RF coil array interfacing cable extending between the interfacing connector of the RF coil array and the MRI system controller unit 210. The controller unit 210 may be associated with and/or may be a non-limiting example of the data processing unit 31 or controller unit 25 in FIG. 1.

The coupling electronics portion 203 may be coupled to the loop portion 201 of the RF coil 202. Herein, the coupling electronics portion 203 may include a decoupling circuit 204, an impedance inverter circuit 206, and a pre-amplifier 208. The decoupling circuit 204 may effectively decouple the RF coil during a transmit operation. Typically, the RF coil 202 in its receive mode may be coupled to a body of a subject being imaged by the MRI apparatus in order to receive echoes of the RF signal transmitted during the transmit mode. If the RF coil 202 is not used for transmission, then it may be necessary to decouple the RF coil 202 from the RF body coil while the RF body coil is transmitting the RF signal. The decoupling of the receive coil from the transmit coil may be achieved using resonance circuits and PIN diodes, microelectromechanical systems (MEMS) switches, or another type of switching circuitry. Herein, the switching circuitry may activate detuning circuits operatively connected to the RF coil 202.

The impedance inverter circuit 206 may form an impedance matching network between the RF coil 202 and the pre-amplifier 208. The impedance inverter circuit 206 is configured to transform a coil impedance of the RF coil 202 into an optimal source impedance for the pre-amplifier 208. The impedance inverter circuit 206 may include an impedance matching network and an input balun. The pre-amplifier 208 receives MR signals from the corresponding RF coil 202 and amplifies the received MR signals. In one example, the pre-amplifier may have a low input impedance that is configured to accommodate a relatively high blocking or source impedance. Additional details regarding the RF coil and associated coupling electronics portion will be explained in more detail below with respect to FIGS. 3 and 4. The coupling electronics portion 203 may be packaged in a very small PCB approximately 2 cm$^2$ in size or smaller. The PCB may be protected with a conformal coating or an encapsulating resin.

The coil-interfacing cable 212, such as an RF coil array interfacing cable, may be used to transmit signals between the RF coils and other aspects of the processing system, for example to control the RF coils and/or to receive information from the RF coils. The RF coil array interfacing cables may be disposed within the bore or imaging space of the MRI apparatus (such as MRI apparatus 10 of FIG. 1) and subjected to electro-magnetic fields produced and used by the MRI apparatus. In MRI systems, coil-interfacing cables, such as coil-interfacing cable 212, may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents.

Thus, coil-interfacing cable 212 may include one or more baluns. In traditional coil-interfacing cables, baluns are positioned with a relatively high density, as high dissipation/voltages may develop if the balun density is too low or if baluns are positioned at an inappropriate location. However, this dense placement may adversely affect flexibility, cost, and performance. As such, the one or more baluns in the coil-interfacing cable may be continuous baluns to ensure no high currents or standing waves, independent of positioning. The continuous baluns may be distributed, flutter, and/or butterfly baluns. Additional details regarding the coil-interfacing cable and baluns will be presented below with respect to FIGS. 14-16.

Figure 3:
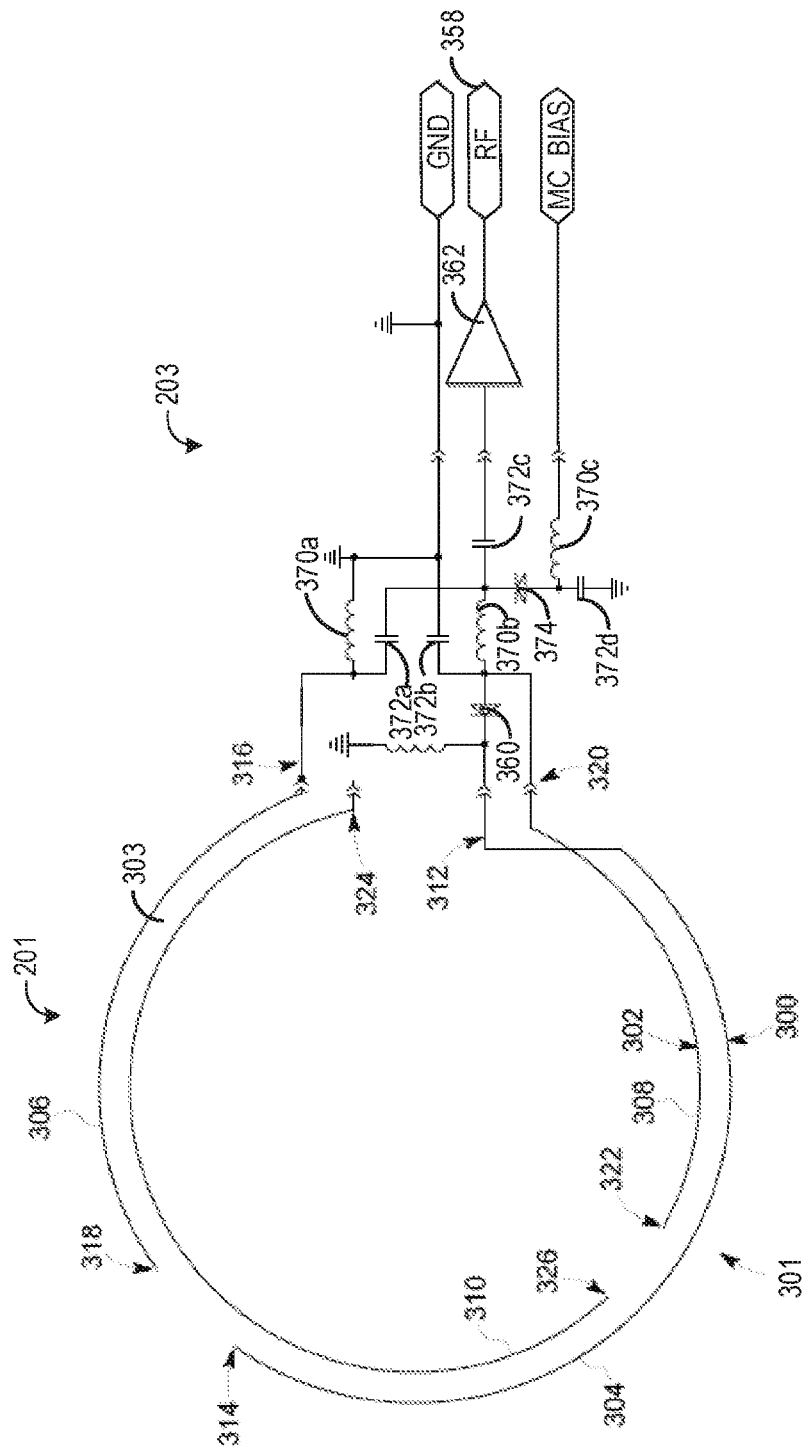
FIG. 3 shows a first example RF coil and associated coupling electronics.

FIG. 3 is a schematic of an RF coil 301 having segmented conductors formed in accordance with an embodiment. RF coil 301 is a non-limiting example of RF coil 202 of FIG. 2 and as such includes loop portion 201 and coupling electronics portion 203 of RF coil 202. The coupling electronics portion allows the RF coil to transmit and/or receive RF signals when driven by the data acquisition unit 124 (shown in FIG. 1). In the illustrated embodiment, the RF coil 301 includes a first conductor 300 and a second conductor 302. The first and second conductors 300, 302 may be segmented such that the conductors form an open circuit (e.g., form a monopole). The segments of the conductors 300, 302 may have different lengths, as is discussed below. The length of the first and second conductors 300, 302 may be varied to achieve a select distributed capacitance, and accordingly, a select resonance frequency.

The first conductor 300 includes a first segment 304 and a second segment 306. The first segment 304 includes a driven end 312 at an interface terminating to coupling electronics portion 203, which will be described in more detail below. The first segment 304 also includes a floating end 314 that is detached from a reference ground, thereby maintaining a floating state. The second segment 306 includes a driven end 316 at the interface terminating to the coupling electronics portion and a floating end 318 that is detached from a reference ground.

The second conductor 302 includes a first segment 308 and a second segment 310. The first segment 308 includes a driven end 320 at the interface. The first segment 308 also includes a floating end 322 that is detached from a reference ground, thereby maintaining a floating state. The second segment 310 includes a driven end 324 at the interface, and a floating end 326 that is detached from a reference ground. The driven end 324 may terminate at the interface such that end 324 is only coupled to the first conductor through the distributed capacitance. The capacitors shown around the loop between the conductors represent the capacitance between the wires.

The first conductor 300 exhibits a distributed capacitance that grows based on the length of the first and second segments 304, 306. The second conductor 302 exhibits a distributed capacitance that grows based on the length of the first and second segments 308, 310. The first segments 304, 308 may have a different length than the second segments 306, 310. The relative difference in length between the first segments 304, 308 and the second segments 306, 310 may be used to produce an effective LC circuit have a resonance frequency at the desired center frequency. For example, by varying the length of the first segments 304, 308 relative to the lengths of the second segments 306, 310, an integrated distributed capacitance may be varied.

In the illustrated embodiment, the first and second conductors 300, 302 are shaped into a loop portion that terminates to an interface. But in other embodiments, other shapes are possible. For example, the loop portion may be a polygon, shaped to conform the contours of a surface (e.g., housing), and/or the like. The loop portion defines a conductive pathway along the first and second conductors. The first and second conductors are void of any discrete or lumped capacitive or inductive elements along an entire length of the conductive pathway. The loop portion may also include loops of varying gauge of stranded or solid conductor wire, loops of varying diameters with varying lengths of the first and second conductors 300, 302, and/or loops of varying spacing between the first and second conductors. For example, each of the first and second conductors may have no cuts or gaps (no segmented conductors) or one or more cuts or gaps (segmented conductors) at various locations along the conductive pathway.

Distributed capacitance (DCAP), as used herein, represents a capacitance exhibited between conductors that grows evenly and uniformly along the length of the conductors and is void of discrete or lumped capacitive components and discrete or lumped inductive components. In the examples herein, the capacitance may grow in a uniform manner along the length of the first and second conductors 300, 302.

A dielectric material 303 encapsulates and separates the first and second conductors 300, 302. The dielectric material 303 may be selectively chosen to achieve a select distributive capacitance. The dielectric material 303 may be based on a desired permittivity E to vary the effective capacitance of the loop portion. For example, the dielectric material 303 may be air, rubber, plastic, or any other dielectric material. In one example, the dielectric material may be polytetrafluoroethylene (pTFE). For example, the dielectric material 303 may be an insulating material surrounding the parallel conductive elements of the first and second conductors 300, 302. Alternatively, the first and second conductors 300, 302 may be twisted upon one another to from a twisted pair cable. As another example, the dielectric material 303 may be a plastic material. The first and second conductors 300, 302 may form a coaxial structure in which the plastic dielectric material 303 separates the first and second conductors. As another example, the first and second conductors may be configured as planar strips.

The coupling electronics portion 203 is operably and communicatively coupled to the RF driver unit 22, the data acquisition unit 124, controller unit 25, and/or data processing unit 31 to allow the RF coil 301 to transmit and/or receive RF signals. In the illustrated embodiment, the coupling electronics portion 203 includes a signal interface 358 configured to transmit and receive the RF signals. The signal interface 358 may transmit and receive the RF signals via a cable. The cable may be a 3-conductor triaxial cable having a center conductor, an inner shield, and an outer shield. The center conductor is connected to the RF signal and pre-amp control (RF), the inner shield is connected to ground (GND), and the outer shield is connected to the multi-control bias (diode decoupling control) (MC_BIAS). A 10V power connection may be carried on the same conductor as the RF signal.

As explained above with respect to FIG. 2, the coupling electronics portion 203 includes a decoupling circuit, impedance inverter circuit, and pre-amplifier. As illustrated in FIG. 3, the decoupling circuit includes a decoupling diode 360. The decoupling diode 360 may be provided with voltage from MC_BIAS, for example, in order to turn decoupling diode 360 on. When on, decoupling diode 360 causes conductor 300 to short with conductor 302, thus causing the coil be off-resonance and hence decouple the coil during a transmit operation, for example.

The impedance inverter circuit includes a plurality of inductors, including first inductor 370a, second inductor 370b, and third inductor 370c; a plurality of capacitors, including first capacitor 372a, a second capacitor 372b, a third capacitor 372c, and a fourth capacitor 372d; and a diode 374. The impedance inverter circuit includes matching circuitry and an input balun. As shown, the input balun is a lattice balun that comprises first inductor 370a, second inductor 370b, first capacitor 372a, and second capacitor 372b. In one example, diode 374 limits the direction of current flow to block RF receive signals from proceeding into decoupling bias branch (MC_BIAS).

The pre-amplifier 362 may be a low input impedance pre-amplifier that is optimized for high source impedance by the impedance matching circuitry. The pre-amplifier may have a low noise reflection coefficient, $\gamma$, and a low noise resistance, Rn. In one example, the pre-amplifier may have a source reflection coefficient of $\gamma$ substantially equal to 0.0 and a normalized noise resistance of Rn substantially equal to 0.0 in addition to the low noise figure. However, γ values substantially equal to or less than 0.1 and Rn values substantially equal to or less than 0.2 are also contemplated. With the pre-amplifier having the appropriate γ and Rn values, the pre-amplifier provides a blocking impedance for RF coil 301 while also providing a large noise circle in the context of a Smith Chart. As such, current in RF coil 301 is minimized, the pre-amplifier is effectively noise matched with RF coil 301 output impedance. Having a large noise circle, the pre-amplifier yields an effective SNR over a variety of RF coil impedances while producing a high blocking impedance to RF coil 301.

In some examples, the pre-amplifier 362 may include an impedance transformer that includes a capacitor and an inductor. The impedance transformer may be configured to alter the impedance of the pre-amplifier to effectively cancel out a reactance of the pre-amplifier, such as capacitance caused by a parasitic capacitance effect. Parasitic capacitance effects can be caused by, for example, a PCB layout of the pre-amplifier or by a gate of the pre-amplifier. Further, such reactance can often increase as the frequency increases. Advantageously, however, configuring the impedance transformer of the pre-amplifier to cancel, or at least minimize, reactance maintains a high impedance (i.e. a blocking impedance) to RF coil 301 and an effective SNR without having a substantial impact on the noise figure of the pre-amplifier. The lattice balun described above may be a non-limiting example of an impedance transformer.

In examples, the pre-amplifier described herein may a low input pre-amplifier. For example, in some embodiments, a "relatively low" input impedance of the preamplifier is less than approximately 5 ohms at resonance frequency. The coil impedance of the RF coil 301 may have any value, which may be dependent on coil loading, coil size, field strength, and/or the like. Examples of the coil impedance of the RF coil 301 include, but are not limited to, between approximately 2 ohms and approximately 10 ohms at 1.5 T magnetic field strength, and/or the like. The impedance inverter circuitry is configured to transform the coil impedance of the RF coil 301 into a relatively high source impedance. For example, in some embodiments, a "relatively high" source impedance is at least approximately 100 ohms and may be greater than 150 ohms.

The impedance transformer may also provide a blocking impedance to the RF coil 301. Transformation of the coil impedance of the RF coil 301 to a relative high source impedance may enable the impedance transformer to provide a higher blocking impedance to the RF coil 301. Exemplary values for such higher blocking impedances include, for example, a blocking impedance of at least 500 ohms, and at least 1000 ohms.

Figure 4:
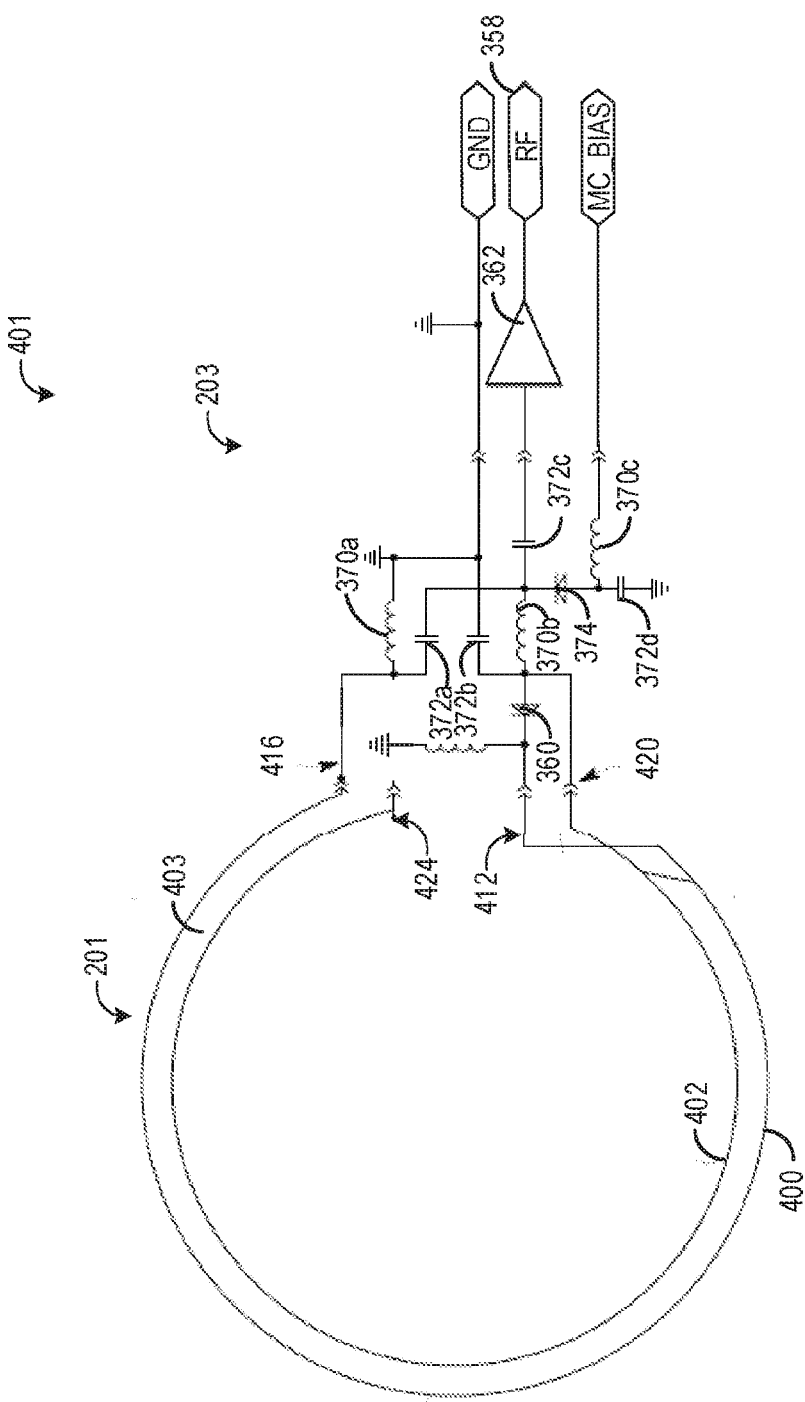
FIG. 4 shows a second example RF coil and associated coupling electronics.

FIG. 4 is a schematic of an RF coil 401 including a loop portion 201 and coupling electronics portion 203 according to another embodiment. The RF coil of FIG. 4 is a non-limiting example of the RF coil and coupling electronics of FIG. 2, and as such includes a loop portion 201 and coupling electronics portion 203. The coupling electronics allows the RF coil to transmit and/or receive RF signals when driven by the data acquisition unit 124 (shown in FIG. 1). The RF coil 401 includes a first conductor 400 in parallel with a second conductor 402. At least one of the first and second conductors 400, 402 are elongated and continuous.

In the illustrated embodiment, the first and second conductors 400, 402 are shaped into a loop portion that terminates to an interface. But in other embodiments, other shapes are possible. For example, the loop portion may be a polygon, shaped to conform the contours of a surface (e.g., housing), and/or the like. The loop portion defines a conductive pathway along the first and second conductors 400, 402. The first and second conductors 400, 402 are void of any discrete or lumped capacitive or inductive components along an entire length of the conductive pathway. The first and second conductors 400, 402 are uninterrupted and continuous along an entire length of the loop portion. The loop portion may also include loops of varying gauge of stranded or solid conductor wire, loops of varying diameters with varying lengths of the first and second conductors 400, 402, and/or loops of varying spacing between the first and second conductors. For example, each of the first and second conductors may have no cuts or gaps (no segmented conductors) or one or more cuts or gaps (segmented conductors) at various locations along the conductive pathway.

The first and second conductors 400, 402 have a distributed capacitance along the length of the loop portion (e.g., along the length of the first and second conductors 400, 402). The first and second conductors 400, 402 exhibit a substantially equal and uniform capacitance along the entire length of the loop portion. Distributed capacitance (DCAP), as used herein, represents a capacitance exhibited between conductors that grows evenly and uniformly along the length of the conductors and is void of discrete or lumped capacitive components and discrete or lumped inductive components. In the examples herein, the capacitance may grow in a uniform manner along the length of the first and second conductors 400, 402. At least one of the first and second conductors 400, 402 are elongated and continuous. In the illustrated embodiment, both the first and second conductors 400, 402 are elongated and continuous. But in other embodiments, only one of the first or second conductors 400, 402 may be elongated and continuous. The first and second conductors 400, 402 form continuous distributed capacitors. The capacitance grows at a substantially constant rate along the length of the conductors 400, 402. In the illustrated embodiment, the first and second conductors 400, 402 form elongated continuous conductors that exhibits DCAP along the length of the first and second conductors 400, 402. The first and second conductors 400, 402 are void of any discrete capacitive and inductive components along the entire length of the continuous conductors between terminating ends of the first and second conductors 400, 402. For example, the first and second conductors 400, 402 do not include any discrete capacitors, nor any inductors along the length of the loop portion.

A dielectric material 403 separates the first and second conductors 400, 402. The dielectric material 403 may be selectively chosen to achieve a select distributive capacitance. The dielectric material 403 may be based on a desired permittivity ϵ to vary the effective capacitance of the loop portion. For example, the dielectric material 403 may be air, rubber, plastic, or any other dielectric material. In one example, the dielectric material may be polytetrafluoroethylene (pTFE). For example, the dielectric material 403 may be an insulating material surrounding the parallel conductive elements of the first and second conductors 400, 402. Alternatively, the first and second conductors 400, 402 may be twisted upon one another to from a twisted pair cable. As another example, the dielectric material 403 may be a plastic material. The first and second conductors 400, 402 may form a coaxial structure in which the plastic dielectric material 403 separates the first and second conductors 400, 402. As another example, the first and second conductors 400, 402 may be configured as planar strips.

The first conductor 400 includes a first terminating end 412 and a second terminating end 416 that terminates at the interface. The first terminating end 412 is coupled to the coupling electronics portion 203. The first terminating end 412 may also be referred to herein as a "drive end." The second terminating end 416 is also referred to herein as a "second drive end."

The second conductor 402 includes a first terminating end 420 and a second terminating end 424 that terminates at the interface. The first terminating end 420 is coupled to the coupling electronics portion 203. The first terminating end 420 may also be referred to herein as a "drive end." The second terminating end 424 is also referred to herein as a "second drive end."

The loop portion 201 of the RF coil 401 is coupled to coupling electronics portion 203. The coupling electronics portion 203 may be the same coupling electronics described above with respect to FIGS. 2 and 3, and hence like reference numbers are given to like components and further description is dispensed with.

As appreciated by FIGS. 3 and 4, the two parallel conductors comprising the loop portion of an RF coil may each be continuous conductors, as illustrated in FIG. 4, or one or both of the conductors may be non-continuous, as illustrated in FIG. 3. For example, both conductors shown in FIG. 3 may include cuts, resulting in each conductor being comprised of two segments. The resulting space between conductor segments may be filled with the dielectric material that encapsulates and surrounds the conductors. The two cuts may be positioned at different locations, e.g., one cut at 135° and the other cut at 225° (relative to where the loop portion interfaces with the coupling electronics). By including discontinuous conductors, the resonance frequency of the coil may be adjusted relative to a coil that includes continuous conductors. In an example, an RF coil that includes two continuous parallel conductors encapsulated and separated by a dielectric, the resonance frequency may be a smaller, first resonance frequency. If that RF coil instead includes one discontinuous conductor (e.g., where one of the conductors is cut and filled with the dielectric material) and one continuous conductor, with all other parameters (e.g., conductor wire gauge, loop diameter, spacing between conductors, dielectric material) being the same, the resonance frequency of the RF coil may be a larger, second resonance frequency. In this way, parameters of the loop portion, including conductor wire gauge, loop diameter, spacing between conductors, dielectric material selection and/or thickness, and conductor segment number and lengths, may be adjusted to tune the RF coil to a desired resonance frequency.

The RF coils presented above with respect to FIGS. 2-4 may be utilized in order to receive MR signals during an MR imaging session. As such, the RF coils of FIGS. 2-4 may be non-limiting examples of RF coil unit 14 of FIG. 1 and may be configured to be coupled to a downstream component of the MRI system, such as a processing system. The RF coils of FIGS. 2-4 may be present in an array of RF coils having various configurations. FIGS. 5-16, described in more detail below, illustrate various embodiments for RF coil arrays and accompanying coil-interfacing cables that may include one or more of the RF coils described above with respect to FIGS. 2-4.

Figure 5:
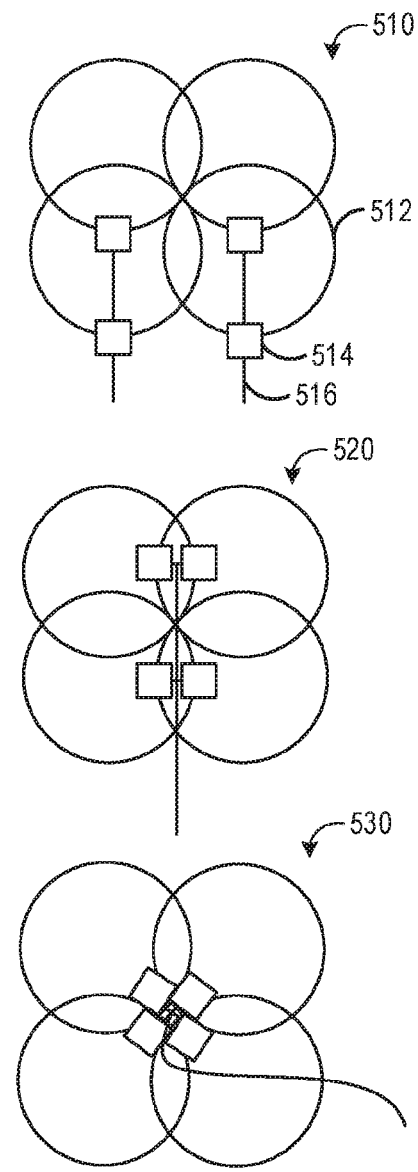
FIG. 5 shows a plurality of example RF coil array configurations.

FIG. 5 shows different arrangements for an RF coil array. First RF coil array 510 includes a coil loop and an electronics unit coupled to each coil loop, and a coil-interfacing cable connected to and extending from each coupling electronics unit. Accordingly, RF coil array 510 includes four coil loops, four electronics units, and four coil-interfacing cables. For example, RF coil array 510 includes a first RF coil comprising a first coil loop 512, a first coupling electronics portion 514, and a first coil-interfacing cable 516. Second RF coil array 520 includes a separate electronics unit for each coil loop, with each electronics unit coupled to a respective coil-interfacing cable. Array 520 includes four coil loops, four electronics units, and four coil-interfacing cables that are budled together in a single grouping of four coil-interfacing cables, and may be referred to as an integrated balun cable harness. For example, the two coil-interfacing cables coupled to the two top electronics units are bundled together, and they are bundled with the two coil-interfacing cables from the two bottom electronics units. Third RF coil array 530 includes a separate electronics unit for each coil loop, with each electronics unit coupled to a respective coil-interfacing cable. Array 530 includes four coil loops, four electronics units, and four coil-interfacing cables that are bundled together in a single grouping of four coil-interfacing cables, and may be referred to as an integrated balun cable harness.

The individual coupling electronics may be housed in a common electronics housing. Each coil loop of the coil array may have respective coupling electronics (e.g., a decoupling circuit, impedance inverter circuit, and pre-amplifier) housed in the housing. In some examples, the common electronics housing may be detachable from the coil loop or RF coil array. In particular, if the individual coupling electronics are configured as in the RF coil array 530 of FIG. 5, the electronics may be placed in a separable assembly and disconnected from the RF coil array. A connector interface could be placed at, for example, the junctions between the conductor loop portions (e.g., the drive ends described above) and the coupling electronics for each individual coupling electronics unit.

The conductor wires and coil loops used in the loop portion of the RF coil or RF coil array may be manufactured in any suitable manner to get the desired resonance frequency for a desired RF coil application. The desired conductor wire gauge, such as 28 or 30 American Wire Gauge (AWG) or any other desired wired gauge may be paired with a parallel conductor wire of the same gauge and encapsulated with a dielectric material using an extrusion process or a three-dimensional (3D) printing or additive manufacturing process. This manufacturing process may be environmentally friendly with low waste and low-cost.

Thus, the RF coil described herein includes a twin lead conductor wire loop encapsulated in a pTFE dielectric that may have no cuts or at least one cut in at least one of the two parallel conductor wires and a miniaturized coupling electronics PCB coupled to each coil loop (e.g., very small coupling electronics PCB approximately the size of 2 cm$^2$ or smaller). The PCBs may be protected with a conformal coating or an encapsulation resin. In doing so, traditional components are eliminated and capacitance is "built in" the integrated capacitor (INCA) coil loops. Interactions between coil elements are reduced or eliminated. The coil loops are adaptable to a broad range of MR operating frequencies by changing the gauge of conductor wire used, spacing between conductor wires, loop diameters, loop shapes, and the number and placement of cuts in the conductor wires.

The coil loops are transparent in PET/MR applications, aiding dose management and signal-to-noise ratios (SNR). The miniaturized coupling electronics PCB includes decoupling circuitry, impedance inverter circuitry with impedance matching circuitry and an input balun, and a pre-amplifier. The pre-amplifier sets new standards in coil array applications for lowest noise, robustness, and transparency. The pre-amplifier provides active noise cancelling to reduce current noise, boost linearity, and improve tolerance to varying coil loading conditions. Additionally, as explained in more detail below, a cable harness with baluns for coupling each of the miniaturized coupling electronics PCBs to the RF coil array connector that interfaces with the MRI system may be provided.

The RF coil described herein is exceptionally lightweight, and may weigh less than 10 grams per coil element versus 45 grams per coil element with General Electric Company's Geometry Embracing Method (GEM) suite of flexible RF coil arrays. For example, a 16-channel RF coil array according to the disclosure may weigh less than 0.5 kg. The RF coil described herein is exceptionally flexible and durable as the coil is extremely simple with very few rigid components and allowing floating overlaps. The RF coil described herein is exceptionally low-cost, e.g., greater than ten times reduction from current technology. For example, a 16-channel RF coil array could be comprised of components and materials of less than $50. The RF coil described herein does not preclude current packaging or emerging technologies and could be implemented in RF coil arrays that do not need to be packaged or attached to a former, or implemented in RF coil arrays that are attached to flexible formers or stretchable materials.

The combination of an INCA coil loop and associated coupling electronics is a single coil element, which is functionally independent and electrically immune to its surrounding environment or neighboring coil elements. As a result, the RF coil described herein performs equally well in low and high-density coil array applications. The exceptional isolation between coil elements allows the overlap between coil elements to be maximized without degrading performance across coil elements. This allows for a higher density of coil elements than is possible with traditional RF coil array designs.

Figure 6:
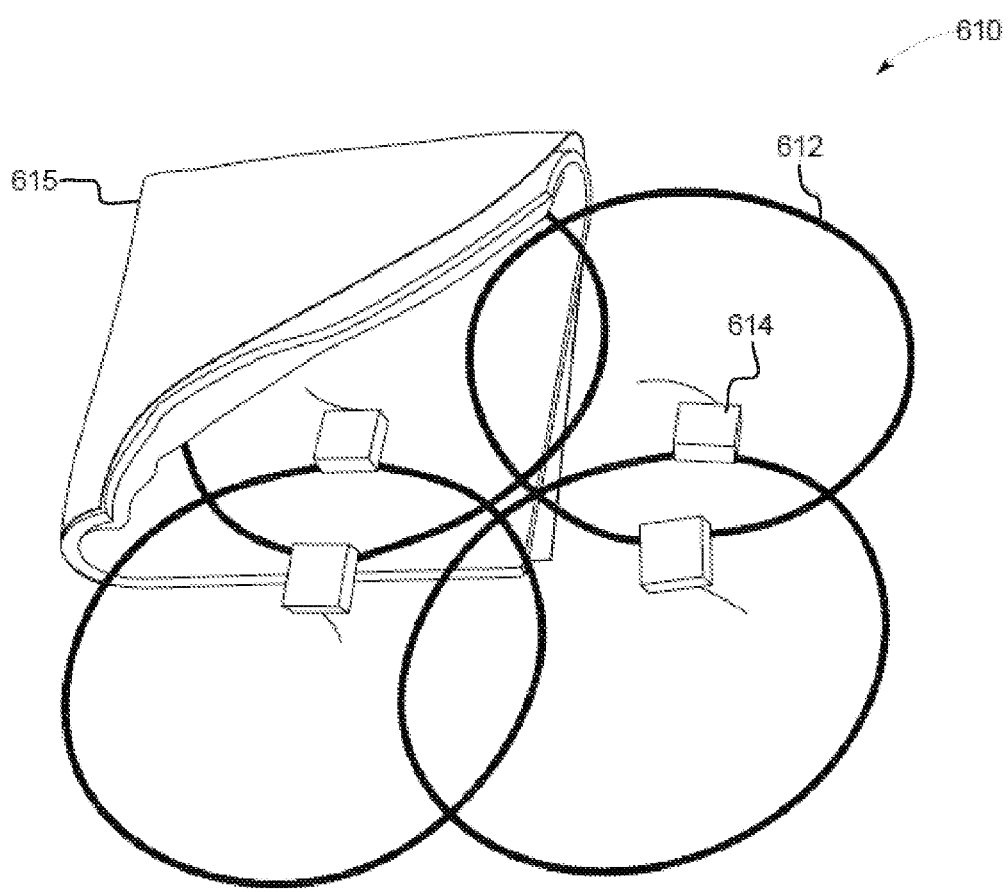
FIG. 6 schematically shows an example RF coil array of the present disclosure.

FIG. 6 shows a flexible, distributed capacitance RF coil array 610. RF coil array 610 includes a plurality of RF coil loops comprised of parallel conductors, without lumped components, and further includes respective miniaturized coupling electronics, as described above with respect to FIGS. 2-4. For example, an RF coil loop of RF coil array 610 includes a coil loop 612 of parallel conductors and associated coupling electronics 614. The RF coil loops may be positioned in an overlapping manner and may be enclosed in virtually any material. As shown, RF coil array 610 may be enclosed in a flexible or stretchable material 615.

In contrast, a traditional RF coil array may include a plurality of RF coil loops that include copper traces on a PCB, which is rigid and maintains the RF coils at fixed positions relative to each other. The RF coils include lumped components (e.g., capacitors, inductors, resistors, etc.) and a relatively large arrangement of coupling electronics, as compared to the coupling electronics of the RF coil array 610. For example, a traditional RF coil array includes a PCB on which copper traces are formed and lumped components are present. The coupling electronics may include bulky and rigid components, such as capacitors, baluns, inductors, resistors, etc. Further, due to the configuration of the traditional RF coil array (e.g., due to heat generation by the RF coil array), a rigid and/or bulky housing material is required. Further, the traditional RF coil array may comprise only a portion of a traditional overall RF coil array element actually used during MR imaging. For example, a traditional overall RF coil array element may include a plurality of separate traditional RF coil arrays, further increasing the size, weight, and cost of a traditional overall RF coil array.

As appreciated by FIG. 6, the coils in RF coil array 610 are not supported by or surrounded by a substrate. While the conductors in the RF coil loops are encapsulated in dielectric material, at least in some examples, no other substrates are present around the entirety of the RF coils. The RF coils may be enclosed in stretchable fabric or other flexible enclosure, but the RF coils may remain flexible in multiple dimensions and may not be fixedly connected to one another. In some examples, the RF coils may be slidably movable relative to each other, such that varying amounts of overlap among coil elements is provided. In contrast, the coil elements of a traditional RF coil array are fixed in position relative to each other and are surrounded by substrate (e.g., PCB). Thus, even when the substrate is flexible, the movement of the coil elements of a traditional RF coil array is limited.

Figure 7:
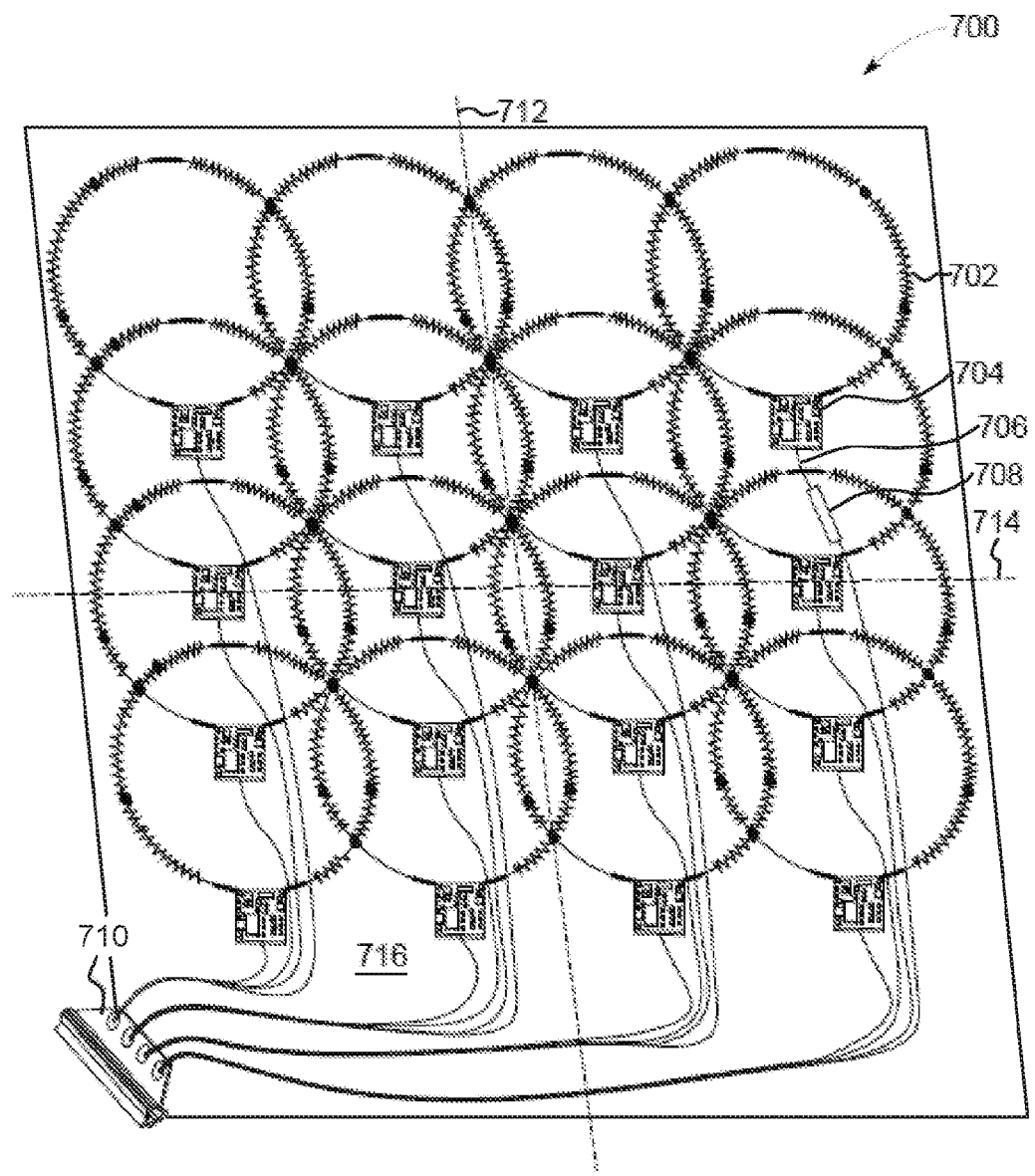
FIG. 7 shows an example RF coil array coupled to a stretchable support.

FIG. 7 shows an example RF coil array 700 including sixteen (16) RF coils attached to a fabric support. Each RF coil of the RF coil array is a non-limiting example of the RF coils described above with respect to FIGS. 2-4 and as such includes an integrated capacitor coil loop 702 and coupling electronics portion 704 directly coupled to each of the coil loops. A coil-interfacing cable (such as cable 706) is connected to and extends from each electronics portion. The coil interfacing cable may be a 3-conductor triaxial cable having a center conductor, an inner shield, and an outer shield. The center conductor is connected to the RF signal and pre-amp control (RF), the inner shield is connected to ground (GND), and the outer shield is connected to the multi-control bias (diode decoupling control) (MC_BIAS). A 10V power connection may be carried on the same conductor as the RF signal and pre-amp control (RF).

The 16 coil-interfacing cables are bundled together and extend to an interfacing connector 710. Each coil-interfacing cable may be coupled to at least one balun (such as balun 708) between each coupling electronics unit 704 and interfacing connector 710 (while only one balun is illustrated in FIG. 7, it is to be understood that each coil-interfacing cable may include a respective balun, at least in some examples). In some examples, the coil-interfacing cables of the RF coil array 700 may include continuous and/or contiguous baluns throughout their length to eliminate the cylinder-shaped lumpy baluns. Interfacing connector 710 may be configured to couple to a processing system or other component of an MRI system via a RF coil array interfacing cable (not shown), for example.

The RF coil loops 702 shown in FIG. 7 may be stitched to a supporting fabric material 716. Even when stitched or otherwise coupled to a support, each RF coil maintains flexibility in multiple dimensions. For example, the RF coil array 700 may flex about a first axis (shown by line 712 of FIG. 7), and may also flex about a second axis (shown by line 714 of FIG. 7).

The RF coils described herein may allow for attachment to and/or incorporation into a variety of different flexible or stretchable support materials and enclosures. The RF coils described herein allow for implementation as wearable coil arrays and stretchable coil arrays, such as in hats, pants, shorts, shirts, bras, mittens, gloves, socks, sleeves for joints (ankle, knee, wrist, elbow, or shoulder), shoulder straps, etc.

Figure 8:
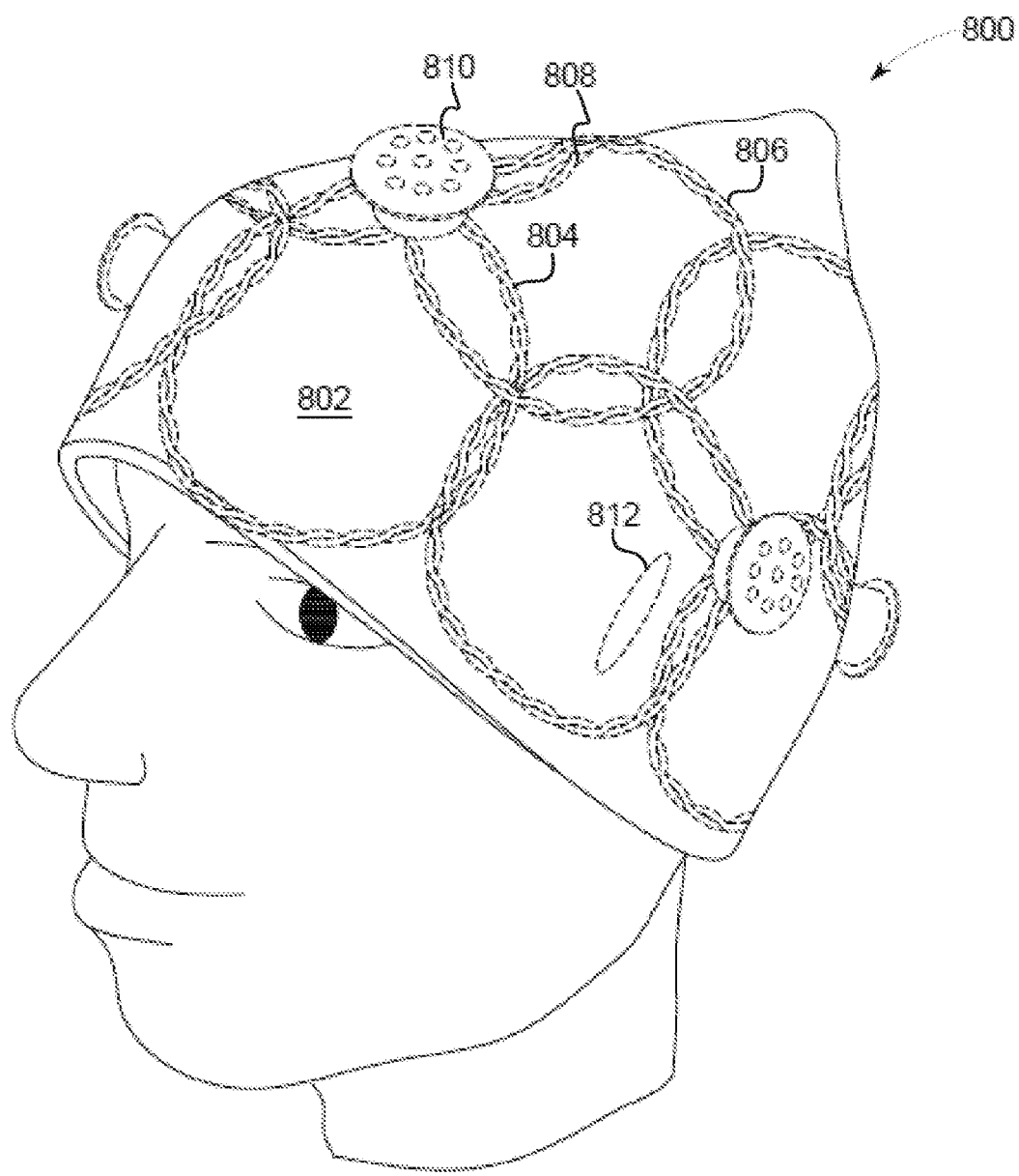
FIG. 8 shows an example RF coil array coupled to a stretchable material.

FIG. 8 shows a stretchable RF coil array 800. The "stretchable" RF coil array relies on the impedance matching interface to reduce loop to loop coupling as well as robustness to loop shape changes. Overlaps may vary from severe, through critical, and even to element underlap.

The RF coil array 800 is attached to a layer of stretchable material, herein in the form of a tight fitting hat 802 (e.g., a "skull cap") for brain imaging, though other configurations are possible. For example, the coils could be adhered, stitched, embedded, or otherwise sewn into or onto other clothing type articles or stretchable sleeves. Compared to a rigid former to hold element positions and overlaps, or a custom element arrangement per head size/shape, the stretchable coil array approach may offer very tight coupling to various shapes without significant RF coil element interaction or degraded performance.

For example, the coils may be coupled to a stretchable material comprising elastomer, polyester, or other stretchable synthetic fabrics, cotton, and so forth. As specific examples, the coils may be coupled to neoprene, dri-fit fabric, spandex, or other stretchable fabric that can fit over feet, ankles, knees, hands, wrists, elbows, torso, shoulders, breasts, neck, head, etc. The stretchable material may be comprised of knitted fabrics that include hard fiber yarn that is non-elastomeric and an elastomeric yarn, for example knitted fabrics having 5 to 20% elastomeric fiber content and from 95 to 80% hard fiber content. In other examples, the stretchable material may be comprised of connected loops of wool, cotton, or other elastomeric and/or non-elastomeric yarns.

As used herein, a "stretchable" material may include the material being capable of being stretched from a first length and/or width to a second length and/or width using a suitable amount of force, such as an amount of force that may be applied by a wearer of the stretchable material. In one example, a stretchable material may be defined as having a threshold stretch force (or less), wherein the stretch force includes the force per unit width required to stretch the material by 10% (or 20%, 50%, or other suitable percentage) of its original length. For example, a stretchable material may have a 10% stretch force of 0.15 kg/cm (0.85 pli) or less, where 0.15 kg/cm force is required to stretch the material by 10% of its original length. The stretchability of the stretchable material may permit the stretchable material to conform to a body of a wearer and may allow the stretchable material to stretch in one or two dimensions when the material is being moved over a part of a body of a wearer (such as a head, elbow, torso, etc.) and may allow the stretchable material to accommodate any normal anatomic range of motion, e.g., bending of an elbow or knee. Once the stretchable material is removed from the part of the body, the stretchable material may return to its non-stretched state.

The stretchable RF coil array 800 includes a plurality of RF coils, including first RF coil 804, second RF coil 806, and third RF coil 808, sewn, glued, or otherwise attached to the layer of stretchable material of hat 802. For example, each RF coil may be coupled to the layer of stretchable material via one or more threads that traverse the layer of stretchable material. Each RF coil includes respective coupling electronics, and more than one set of coupling electronics may be housed in a single housing. As shown, the coupling electronics for first RF coil 804, second RF coil 806, and third RF coil 808 may be housed in a common electronics housing 810. The coil-interfacing cables configured to couple to each set of coupling electronics may be detachable, as shown, or may be fixedly coupled.

In the example stretchable RF coil array illustrated herein, the material on which the RF coils are attached may be stretchable, but the RF coils themselves may have little or no stretch. In such a configuration, the overlap distance between the RF coils may change as the underlying material is stretched, but the RF coils may maintain a relatively fixed circumferential distance. For example, when the stretchable material is not being stretched, a center of a first RF coil coupled to the stretchable material may be separated from a center of an adjacent, second RF coil by a first overlap distance. Then, once the stretchable material is pulled over a designated body part (e.g., the head of the subject being imaged), the stretchable material may stretch such that the center of the first RF coil is separated from the center of the second RF coil by a second overlap distance that is larger than the first overlap distance. The diameter of each of the first RF coil and the second RF coil may remain the same due to the RF coils not being stretchable.

However, even when the RF coils are not made from stretchable material, the RF coils may deform to a degree, e.g., deform from circular to an elliptical shape. Further, it may possible in some examples for the paralleled conductors forming the loop portion of each RF coil to be stretchable to enable an entirety of the stretchable RF coil array to stretch (e.g., both the RF coils themselves and the material to which they are attached may stretch). In such a configuration, the overlap distance between the RF coils may change as the underlying material is stretched, and the shape of the RF coils may also change as the underlying material is stretched.

In some examples, RF coil arrays may include markers that are visible to an operator and/or to the imaging system (e.g., fiduciary markers that may be present on the RF coils themselves or on the material to which the RF coils are attached). Such markers may enable an operator to ensure a particularly coil array has been placed on a desired portion of patient anatomy in a designated position and/or orientation, for example. An example marker 812 is illustrated in FIG. 8. An operator may position the coil array on a patient's head such that marker 812 aligns with an ear of the patient, for example.

However, if the coil array is a stretchable coil array, as is the stretchable array 800 of FIG. 8, the marker itself may stretch. In some examples, the extent of the stretching of the coil array may be determined by a change in size of the marker. For example, marker 812 may have a first length and a first width when the array 800 is not positioned on a patient. Then, when the array is positioned on a patient, the marker 812 may have an adjusted second length and/or an adjusted second width, and the overall extent of the stretching of the coil array may be determined from the change in the marker length and/or width. The extent of the stretching of the array may indicate the level of overlap among at least some of the RF coils of the array, at least in some examples. The operator may use this information as an input to the imaging system processor and/or the imaging system may be able to automatically detect the extent of the stretching of the array. The imaging system may adjust various imaging parameters based on the amount of stretching/overlap of the array/coils. For example, if the level of coil overlap is relatively low (e.g., the coils do not overlap), parallel imaging may be performed, while if the level of overlap between the coils is relatively high, non-parallel imaging may be performed. In some examples, image reconstruction may be adjusted based on the level of coil overlap and/or stretching of the array. In still further examples, where a large amount of stretching is expected, the marker may be sized and/or positioned such that the target array placement information is conveyed by the marker in the stretched state.

Thus, by utilizing wires with distributed capacitors, minimal material impedes the forming of the coil to anatomy. The low loop to loop capacitance and the high impedance interfacing allows overlaps to vary, thus allowing elements to slide over each other as the package is stretched. Utilizing a preamplifier with very large noise figure and gain circles allows performance to be maintained as the coil element (loop) is elongated or distorted. The RF coils described herein have no need to control overlaps or maintain loop shape to get good element to element isolation, which allows a coil array to stretch and adapt to various anatomy shapes and sizes. Such an RF coil array configuration allows for very close coupling to patients varying size anatomy for best image quality, and can provide a single coil array optimized for many situations.

Figure 9:
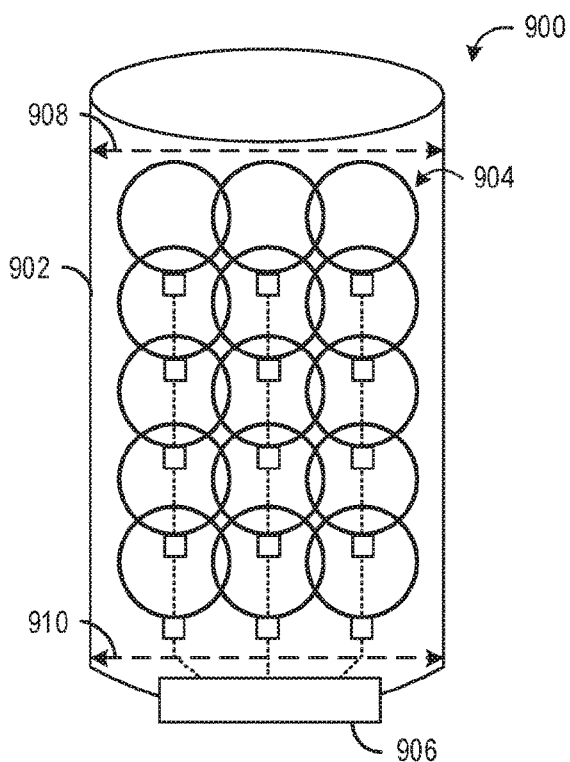
FIGS. 9 and 10 show another example RF coil array coupled to a stretchable material.
Figure 10:
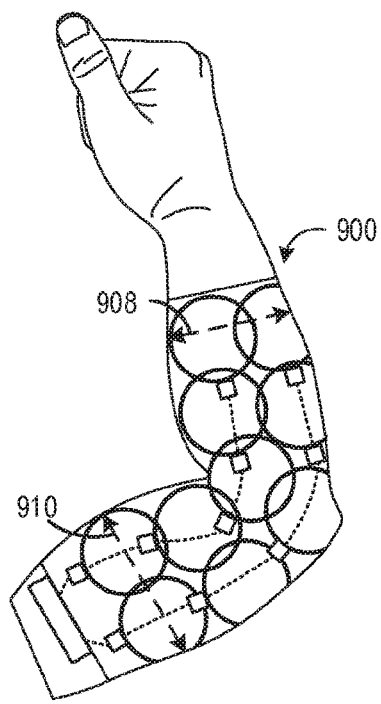

FIGS. 9 and 10 show another example stretchable RF coil array 900. Stretchable RF coil array 900 is configured to be placed over an arm or leg of an imaging subject, for example, and as such includes a stretchable material 902 shaped as a cylinder (with a hollow bore in the middle of the cylinder). The stretchable material 902 may be continuous and/or unitary, such that the stretchable RF coil array 900 may be slid over a suitable body part without engaging or disengaging any fastening mechanisms (e.g., similar to a sleeve or pant leg). The stretchable material 902 may be similar to the stretchable material described above with respect to FIG. 8. The stretchable RF coil array 900 includes a plurality of RF coils 904, which may be similar to the RF coils described above with respect to FIGS. 2-7. The stretchable RF coil array 900 includes an interfacing connector 906 coupled to each RF coil via a respective coil-interfacing cable. FIG. 9 shows the plurality of RF coils including 15 RF coils, but it is to be understood that more or fewer RF coils are possible and that the RF coils may extend around the sides and/or back of the stretchable RF coil array 900.

As mentioned above, the stretchable RF coil array 900 may be shaped as a cylinder/sleeve. As shown in FIG. 9, when the stretchable RF coil array 900 is not being worn by a subject, the stretchable RF coil array 900 may have a width that is relatively constant along a length of the stretchable RF coil array 900. For example, a first width 908 at a top of the stretchable RF coil array may be equal to a second width 910 at a bottom of the stretchable RF coil array, and each RF coil may be spaced apart from adjacent RF coils by a relatively uniform amount. Due to the stretchable nature of the stretchable material 902, the relative spacing of the RF coils may change when the stretchable RF coil array 900 is worn by a subject and the stretchable material 902 is stretched. As shown in FIG. 10, the stretchable material 902 may stretch when the stretchable RF coil array 900 is worn on an arm of a subject. As a result, the relative widths of the cylinder/sleeve may change as well as the relative spacing between RF coils. In FIG. 10, the top portion of the stretchable RF coil array 900 is being worn over a forearm of the subject while the bottom portion of the stretchable RF coil array 900 is being worn over the bicep of the subject. Thus, the bottom portion may stretch more than the top portion, and the width 910 may be larger than the width 908. Further, as appreciated by FIG. 10, the stretchable RF coil array 900 may accommodate anatomical range of motion, e.g., allow bending of an elbow of the subject.

Figure 11:
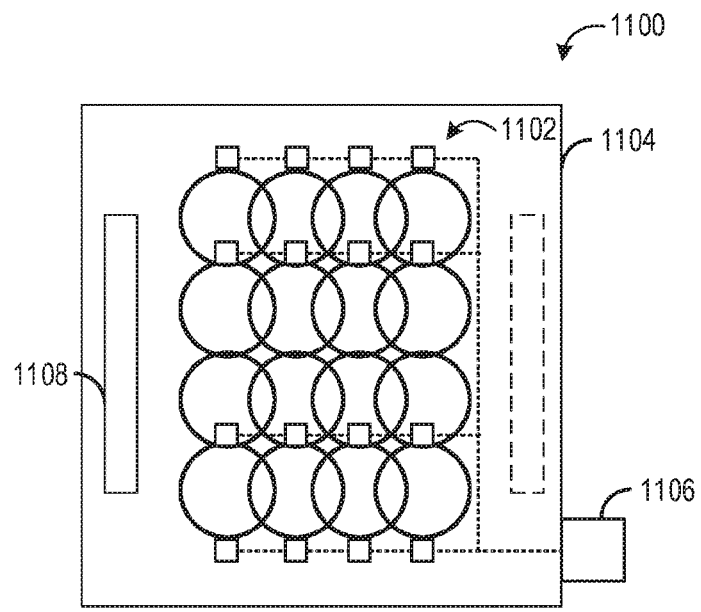
FIG. 11 shows another example RF coil array coupled to a stretchable material.

FIG. 11 shows another example stretchable RF coil array 1100. The stretchable RF coil array 1100 may be configured similarly to a blood-pressure cuff and as such includes a stretchable layer of material 1104 shaped as a rectangle or square (although other shapes are possible without departing from the scope of this disclosure). The stretchable layer of material 1104 may be similar to the materials described above with respect to FIG. 8. A plurality of RF coils 1102 are coupled to a first side of the stretchable layer of material 1104 (e.g., via stitching, adhesive, or other mechanism). The plurality of RF coils 1102 may include 15 RF coils, but in other examples the plurality of RF coils 1102 may include more or fewer RF coils. Each RF coil includes a loop portion, coupling electronics portion, and coil interfacing cable, similar the RF coils described above with respect to FIGS. 2-7. Each coil interfacing cable extends to an interfacing connector 1106 that is configured to couple the plurality of RF coils to a suitable component of an MRI system, such as a processing or data acquisition unit of the MRI system.

The stretchable RF coil array 1100 includes a fastening mechanism to hold the stretchable RF coil array in place (e.g., around an arm or leg of an imaging subject). As shown, the stretchable RF coil array includes a hook-and-loop fastener including a first fastener 1108 coupled to the first side of the stretchable layer of material and a second, complementary fastener (shown by the dashed box) coupled to a second, opposite side of the stretchable layer of material. When the stretchable RF coil array 1100 is wrapped around the imaging subject, the first and second fasteners may come into face-sharing contact and the complementary fasteners may engage. While not shown in FIG. 11, in some examples an outer layer of material may extend over the plurality of RF coils 1102. In such an example, the first fastener 1108 may be located on the outer layer of material.

Figure 12:
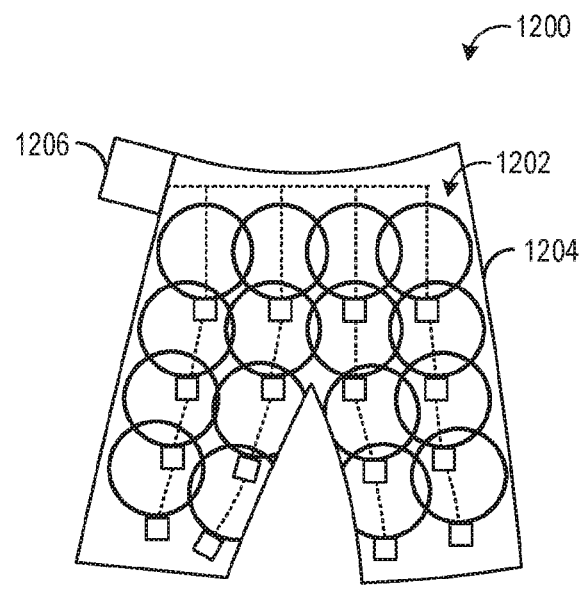
FIG. 12 shows another example RF coil array coupled to a stretchable material.

FIG. 12 shows another example stretchable RF coil array 1200. The stretchable RF coil array 1200 may be configured similarly to a pair of bicycle shorts and as such includes a stretchable layer of material 1204 shaped to accommodate a torso, pelvic region, and upper legs of an imaging subject (although other shapes are possible without departing from the scope of this disclosure). The stretchable layer of material 1204 may be similar to the materials described above with respect to FIG. 8. A plurality of RF coils 1202 are coupled to a first side of the stretchable layer of material 1204 (e.g., via stitching, adhesive, or other mechanism). The plurality of RF coils 1202 may include 15 RF coils, but in other examples the plurality of RF coils 1202 may include more or fewer RF coils, and may extend around all sides of the stretchable layer of material. Each RF coil includes a loop portion, coupling electronics portion, and coil interfacing cable, similar the RF coils described above with respect to FIGS. 2-7. Each coil interfacing cable extends to an interfacing connector 1206 that is configured to couple the plurality of RF coils to a suitable component of an MRI system, such as a processing or data acquisition unit of the MRI system. While not shown in FIG. 12, in some examples an outer layer of material may extend over the plurality of RF coils 1202.

Thus, the stretchable RF coil array 1200 may be configured as a pair of shorts to be pulled over the legs of an imaging subject to position RF coils around the legs, pelvic region, and/or torso of the subject. The stretchable material may stretch to accommodate different body parts and different sized subjects, allowing the RF coils to be positioned in close proximity to the imaging subject, even in areas that may be harder to image with traditional RF coils (e.g., the pelvic region). Similar configurations may be applied to other types of clothing, such as shirts, socks, etc.

Figure 13A:
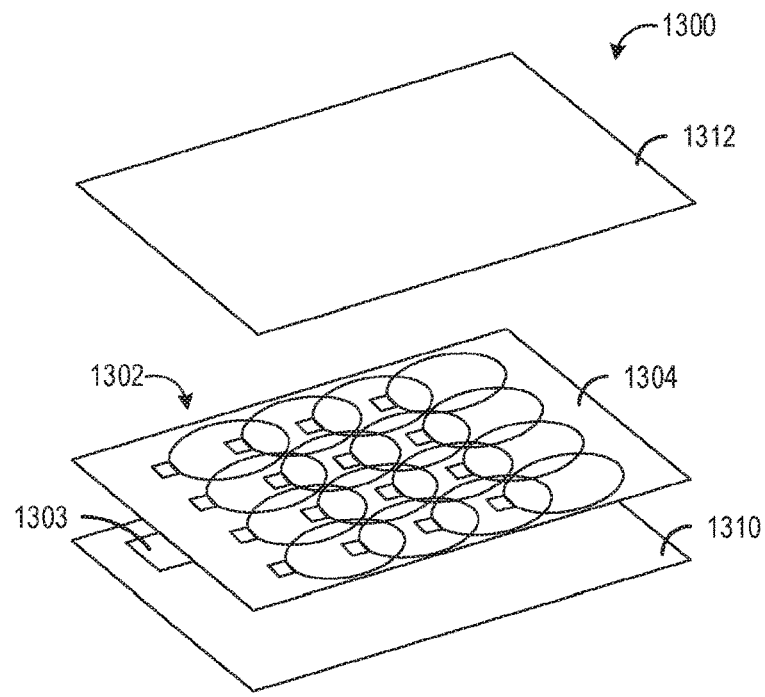
FIG. 13A shows an example packaged stretchable RF coil array.
Figure 13B:
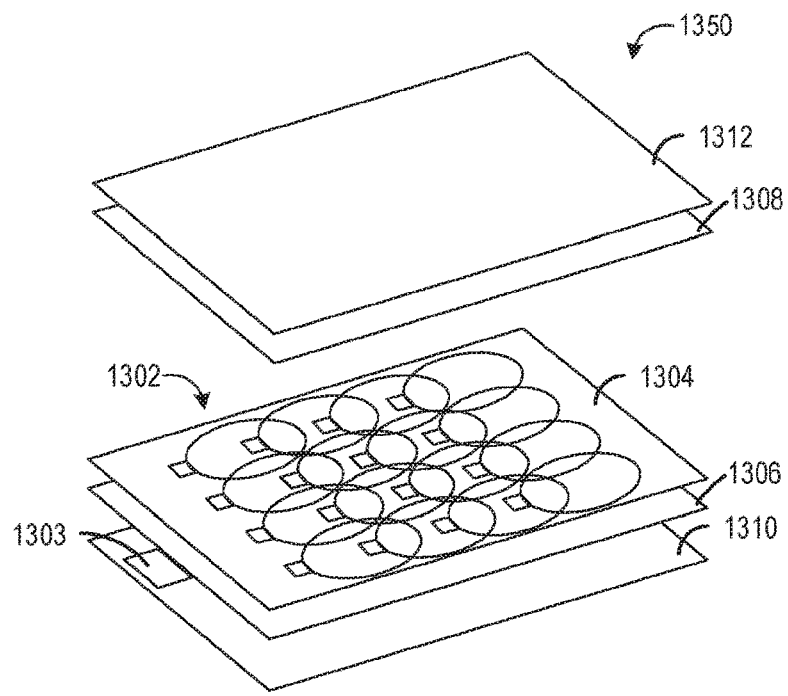
FIG. 13B shows another example packaged stretchable RF coil array.

FIGS. 13A and 13B illustrate examples of packaged RF coil arrays that include the RF coils according to the disclosure. FIG. 13A shows an exploded view of a packaged RF coil array 1300 that includes a flexible housing material enclosing an RF coil array. An interfacing connector 1303 is provided to allow the RF coil array to be coupled or connected to a controller unit or other processing system via a RF coil array interfacing cable. In some examples, the flexible housing material may be stretchable, as described above.

The packaged RF coil array includes a coil array 1302, herein including 16 RF coils each having a miniaturized electronics PCB, as described above with respect to FIGS. 2-7. Each RF coil of the RF coil array is coupled to a section of flexible and/or stretchable fabric material 1304, via stitching or other attachment mechanism. An outer enclosure comprising a first section 1310 and a second section 1312 of material sandwiches the RF coil array and attached material. The material of the outer enclosure may be DARTEX® or other suitable material that is cleanable, thus enabling use of the RF coil array in clinical healthcare applications.

FIG. 13B shows an exploded view 1350 of the packaged RF coil array of FIG. 13A, but with the addition of an inner enclosure. Sandwiching the RF coil array and attached material is an inner enclosure comprising a first section 1306 and second section 1308 of material. The material of the inner enclosure may be NOMEX® or other suitable material that provides padding, spacing, and/or flame retardant properties and/or the material may be stretchable, such as spandex. While FIGS. 13A and 13B illustrate a sheet-like coil array, in some examples the coil array may be configured as a stretchable sleeve, hat, shirt, or other configuration similar in nature to an article of clothing, for example, to enable the stretchable coil array to closely conform to patient anatomy. In such an example, the inner and/or outer enclosures of the coil array illustrated in FIGS. 13A and 13B may be joined together along the short ends or long ends to create a sleeve-type configuration, for example.

As mentioned previously, the RF coil array of the present disclosure may be coupled to a RF coil array interfacing cable that includes contiguous, distributed baluns or common-mode traps in order to minimize high currents or standing waves, independent of positioning. High stress areas of the RF coil array interfacing cable may be served by several baluns. Additionally, the thermal load maybe shared through a common conductor. The inductance of the central path and return path of the RF coil array interfacing cables are not substantially enhanced by mutual inductance, and therefore are stable with geometry changes. Capacitance is distributed and not substantially varied by geometry changes. Resonator dimensions are ideally very small, but in practice may be limited by blocking requirements, electric and magnetic field intensities, local distortions, thermal and voltage stresses, etc.

Figure 14:
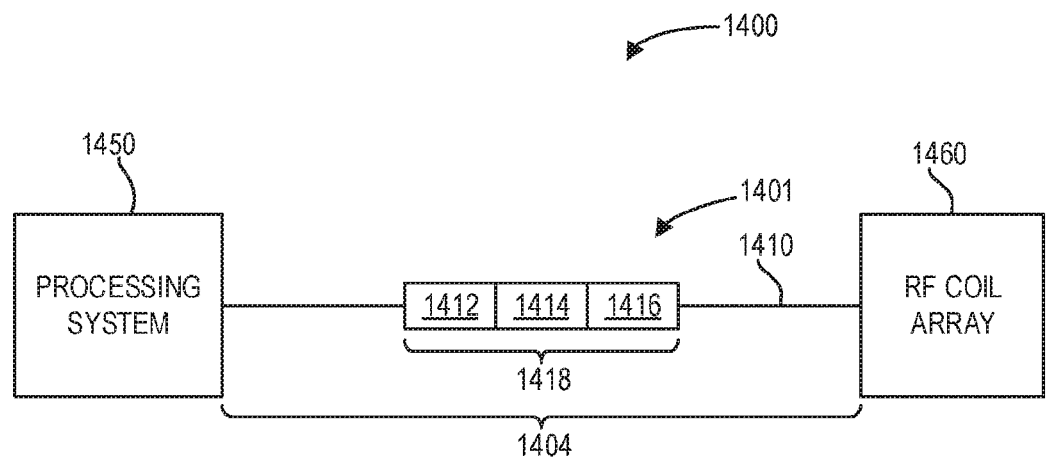
FIG. 14 schematically shows an example RF coil array interfacing cable including a plurality of continuous and/or contiguous common mode traps positioned between a processing system and an RF coil array of a MRI system.

FIG. 14 illustrates a block schematic diagram of a continuous common mode trap assembly 1400 formed in accordance with various embodiments. The common mode trap assembly 1400 may be configured, for example, for use in an MRI system, such as the MRI apparatus 10 described herein above. For example, in the illustrated embodiment, the common mode trap assembly 1400 is configured as a transmission cable 1401 configured for transmission of signals between a processing system 1450 and a RF coil array 1460 of an MRI system. Transmission cable 1401 is a non-limiting example of a RF coil array interfacing cable 212, processing system 1450 is a non-limiting example of controller unit 210, and RF coil array 1460 is a non-limiting example of a plurality of RF coils 202 and coupling electronics portion 203 of FIG. 2.

In the illustrated embodiment, the transmission cable 1401 (or RF coil array interfacing cable) includes a central conductor 1410 and plural common mode traps 1412, 1414, 1416. It may be noted that, while the common mode traps 1412, 1414, and 1416 are depicted as distinct from the central conductor 1410, in some embodiments, the common mode traps 1412, 1414, 1416 may be integrally formed with or as a part of the central conductor 1410.

The central conductor 1410 in the illustrated embodiment has a length 1404, and is configured to transmit a signal between the MRI RF coil array 1460 and at least one processor of an MRI system (e.g., processing system 1450). The central conductor 1410 may include one or more of a ribbon conductor, a wire, or a coaxial cable bundle, for example. The length 1404 of the depicted central conductor 1410 extends from a first end of the central conductor 1410 (which is coupled to the processing system 1450) to a second end of the central conductor 1410 (which is coupled to the RF coil array 1460). In some embodiments, the central conductor may pass through a central opening of the common mode traps 1412, 1414, 1416.

The depicted common mode traps 1412, 1414, 1416 (which may be understood as cooperating to form a common mode trap unit 1418), as seen in FIG. 14, extend along at least a portion of the length 1404 of the central conductor 1410. In the illustrated embodiment, common mode traps 1412, 1414, 1416 do not extend along the entire length 1404. However, in other embodiments, the common mode traps 1412, 1414, 1416 may extend along the entire length 1404, or substantially along the entire length 1404 (e.g., along the entire length 1404 except for portions at the end configured to couple, for example, to a processor or RF coil array). The common mode traps 1412, 1414, 1416 are disposed contiguously. As seen in FIG. 14, each of the common mode traps 1412, 1414, 1416 is disposed contiguously to at least one other of the common mode traps 1412, 1414, 1416. As used herein, contiguous may be understood as including components or aspects that are immediately next to or in contact with each other. For example, contiguous components may be abutting one another. It may be noted that in practice, small or insubstantial gaps may be between contiguous components in some embodiments. In some embodiments, an insubstantial gap (or conductor length) may be understood as being less than $1/40^{th}$ of a wavelength of a transmit frequency in free space. In some embodiments, an insubstantial gap (or conductor length) may be understood as being two centimeters or less. Contiguous common mode traps, for example, have no (or insubstantial) intervening gaps or conductors therebetween that may be susceptible to induction of current from a magnetic field without mitigation provided by a common mode trap.

For example, as depicted in FIG. 14, the common mode trap 1412 is contiguous to the common mode trap 1414, the common mode trap 1414 is contiguous to the common mode trap 1412 and the common mode trap 1416 (and is interposed between the common mode trap 1412 and the common mode trap 1416), and the common mode trap 1416 is contiguous to the common mode trap 1414. Each of the common mode traps 1412, 1414, 1416 are configured to provide an impedance to the receive transmitter driven currents of an MRI system. The common mode traps 1412, 1414, 1416 in various embodiments provide high common mode impedances. Each common mode trap 1412, 1414, 1416, for example, may include a resonant circuit and/or one or more resonant components to provide a desired impedance at or near a desired frequency or within a target frequency range. It may be noted that the common mode traps 1412, 1414, 1416 and/or common mode trap unit 1418 may also be referred to as chokes or baluns by those skilled in the art.

In contrast to systems having separated discrete common mode traps with spaces therebetween, various embodiments (e.g., the common mode trap assembly 1400) have a portion over which common mode traps extend continuously and/or contiguously, so that there are no locations along the portion for which a common mode trap is not provided. Accordingly, difficulties in selecting or achieving particular placement locations of common mode traps may be reduced or eliminated, as all locations of interest may be included within the continuous and/or contiguous common mode trap. In various embodiments, a continuous trap portion (e.g., common mode trap unit 1418) may extend along a length or portion thereof of a transmission cable. The continuous mode trap portion may be formed of contiguously joined individual common mode traps or trap sections (e.g., common mode traps 1412, 1414, 1416). Further, contiguous common mode traps may be employed in various embodiments to at least one of lower the interaction with coil elements, distribute heat over a larger area (e.g., to prevent hot spots), or help ensure that blocking is located at desired or required positions. Further, contiguous common mode traps may be employed in various embodiments to help distribute voltage over a larger area. Additionally, continuous and/or contiguous common mode traps in various embodiments provide flexibility. For example, in some embodiments, common mode traps may be formed using a continuous length of conductor(s) (e.g., outer conductors wrapped about a central conductor) or otherwise organized as integrally formed contiguous sections. In various embodiments, the use of contiguous and/or continuous common mode traps (e.g., formed in a cylinder) provide for a range of flexibility over which flexing of the assembly does not substantially change the resonant frequency of the structure, or over which the assembly remains on frequency as it is flexed.

It may be noted that the individual common mode traps or sections (e.g., common mode traps 1412, 1414, 1416) in various embodiments may be constructed or formed generally similarly to each other (e.g., each trap may be a section of a length of tapered wound coils), but each individual trap or section may be configured slightly differently than other traps or sections. For example, in some embodiments, each common mode trap 1412, 1414, 1416 is tuned independently. Accordingly, each common mode trap 1412, 1414, 1416 may have a resonant frequency that differs from other common mode traps of the same common mode trap assembly 1400.

Alternatively or additionally, each common mode trap may be tuned to have a resonant frequency near an operating frequency of the MRI system. As used herein, a common mode trap may be understood as having a resonant frequency near an operating frequency when the resonant frequency defines or corresponds to a band that includes the operating frequency, or when the resonant frequency is close enough to the operating frequency to provide on-frequency blocking, or to provide a blocking impedance at the operating frequency.

Further additionally or alternatively, each common mode trap may be tuned to have a resonant frequency below an operating frequency of the MRI system (or each common mode trap may be tuned to have resonant frequency above an operating frequency of the MRI system). With each trap having a frequency below (or alternatively, with each trap having a frequency above) the operating frequency, the risk of any of the traps canceling each other out (e.g., due to one trap having a frequency above the operating frequency and a different trap having a frequency below the operating frequency) may be eliminated or reduced. As another example, each common mode trap may be tuned to a particular band to provide a broadband common mode trap assembly.

In various embodiments, the common mode traps may have a two (2D) or three-dimensional (3D) butterfly configuration to counteract magnetic field coupling and/or local distortions.

Figure 15:
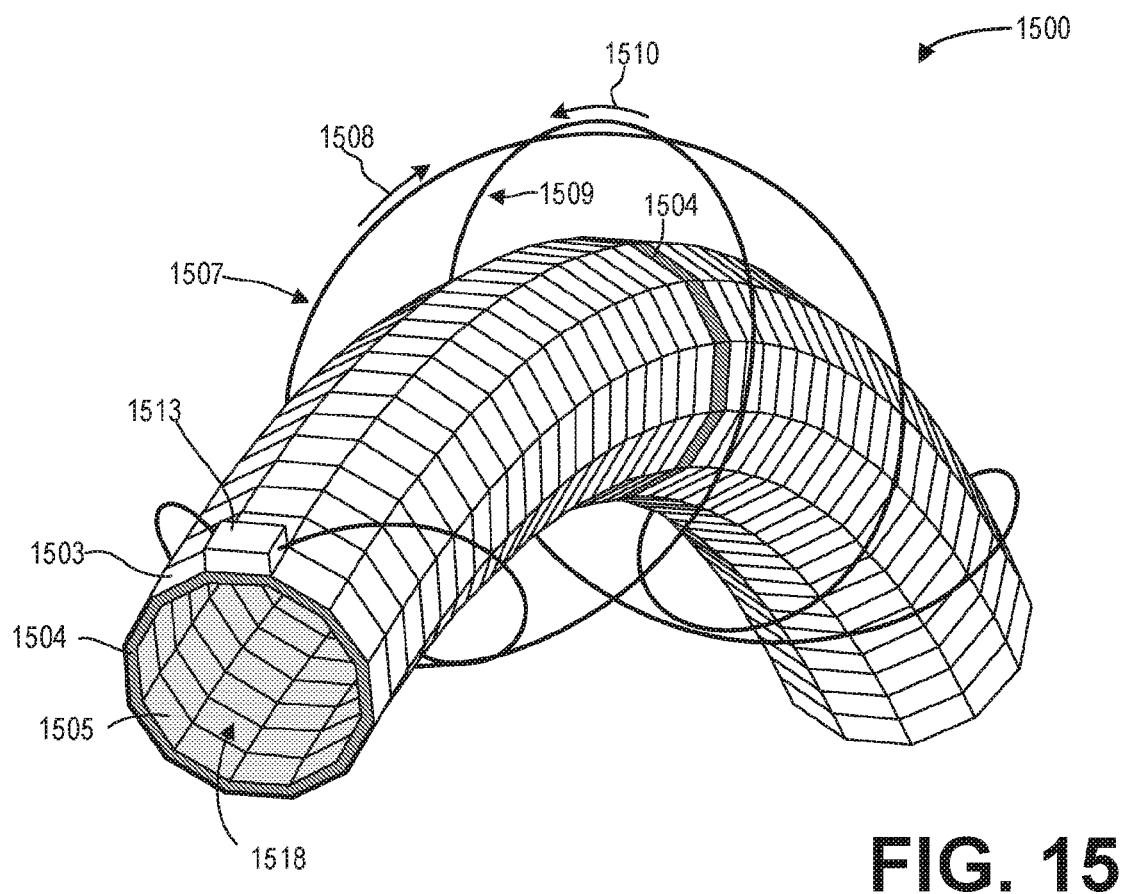
FIGS. 15 and 16 schematically show example RF coil array interfacing cables including a plurality of continuous and/or contiguous common mode traps.

FIG. 15 is a perspective view of a RF coil array interfacing cable 1500 including a plurality of continuous and/or contiguous common mode traps according to an embodiment of the disclosure. The RF coil array interfacing cable 1500 includes an outer sleeve or shield 1503, a dielectric spacer 1504, an inner sleeve 1505, a first common mode trap conductor 1507, and a second common mode trap conductor 1509.

The first common mode trap conductor 1507 is wrapped in a spiral about the dielectric spacer 1504, or wrapped in a spiral at a tapering distance from a central conductor (not shown) disposed within the bore 1518 of the RF coil array interfacing cable 1500, in a first direction 1508. Further, the second common mode trap conductor 1509 is wrapped in a spiral about the dielectric spacer 1504, or wrapped in a spiral at a tapering distance from the central conductor disposed within the bore 1518, in a second direction 1510 that is opposite to the first direction 1508. In the illustrated embodiment, the first direction 1508 is clockwise and the second direction 1510 is counter-clockwise.

The conductors 1507 and 1509 of the RF coil array interfacing cable 1500 may comprise electrically-conductive material (e.g., metal) and may be shaped as ribbons, wires, and/or cables, for example. In some embodiments, the counterwound or outer conductors 1507 and 1509 may serve as a return path for a current passing through the central conductor. Further, in various embodiments, the counterwound conductors 1507 and 1509 may cross each other orthogonally (e.g., a center line or path defined by the first common mode trap conductor 1507 is perpendicular to a center line or path defined by the second common mode trap conductor 1509 as the common mode trap conductors cross paths) to eliminate, minimize, or reduce coupling between the common mode trap conductors.

It may be further noted that in various embodiments the first common mode trap conductor 1507 and the second common mode trap conductor 1509 are loosely wrapped about the dielectric spacer 1504 to provide flexibility and/or to reduce any binding, coupling, or variation in inductance when the RF coil array interfacing cable 1500 is bent or flexed. It may be noted that the looseness or tightness of the counterwound outer conductors may vary by application (e.g., based on the relative sizes of the conductors and dielectric spacer, the amount of bending or flexing that is desired for the common mode trap, or the like). Generally, the outer or counterwound conductors should be tight enough so that they remain in the same general orientation about the dielectric spacer 1504, but loose enough to allow a sufficient amount of slack or movement during bending or flexing of the RF coil array interfacing cable 1500 to avoid, minimize, or reduce coupling or binding of the counterwound outer conductors.

In the illustrated embodiment, the outer shielding 1503 is discontinuous in the middle of the RF coil array interfacing cable 1500 to expose a portion of the dielectric spacer 1504 which in some embodiments is provided along the entire length of the RF coil array interfacing cable 1500. The dielectric spacer 1504, may be comprised, as a non-limiting example, of Teflon or another dielectric material. The dielectric spacer 1504 functions as a capacitor and thus may be tuned or configured to provide a desired resonance. It should be appreciated that other configurations for providing capacitance to the RF coil array interfacing cable 1500 are possible, and that the illustrated configurations are exemplary and non-limiting. For example, discrete capacitors may alternatively be provided to the RF coil array interfacing cable 1500.

Further, the RF coil array interfacing cable 1500 includes a first post 1513 and a second post (not shown) to which the first common mode trap conductor 1507 and the second common mode trap conductor 1509 are fixed. To that end, the first post 1513 and the second post are positioned at the opposite ends of the common mode trap, and are fixed to the outer shielding 1503. The first post 1513 and the second post ensure that the first and second common mode trap conductors 1507 and 1509 are positioned close to the outer shielding 1503 at the ends of the RF coil array interfacing cable 1500, thereby providing a tapered butterfly configuration of the counterwound conductors as described further herein.

The tapered butterfly configuration includes a first loop formed by the first common mode trap conductor 1507 and a second loop formed by the second common mode trap conductor 1509, arranged so that an induced current (a current induced due to a magnetic field) in the first loop 1507 and an induced current in the second loop 1509 cancel each other out. For example, if the field is uniform and the first loop 1507 and the second loop 1509 have equal areas, the resulting net current will be zero. The tapered cylindrical arrangement of the loops 1507 and 1509 provide improved flexibility and consistency of resonant frequency during flexing relative to two-dimensional arrangements conventionally used in common mode traps.

Generally, a tapered butterfly configuration as used herein may be used to refer to a conductor configuration that is flux cancelling, for example including at least two similarly sized opposed loops that are symmetrically disposed about at least one axis and are arranged such that currents induced in each loop (or group of loops) by a magnetic field tends to cancel out currents induced in at least one other loop (or group of loops). For example, with reference to FIG. 14, in some embodiments, counterwound conductors (e.g., conductors wound about a central member and/or axis in opposing spiral directions) may be spaced a distance radially from the central conductor 1410 to form the common mode traps 1412, 1414, 1416. As depicted in FIG. 15, the radial distance may be tapered towards the end of the common mode traps to reduce or altogether eliminate fringe effects. In this way, the common mode traps 1412, 1414, 1416 may be continuously or contiguously positioned without substantial gaps therebetween.

Figure 16:
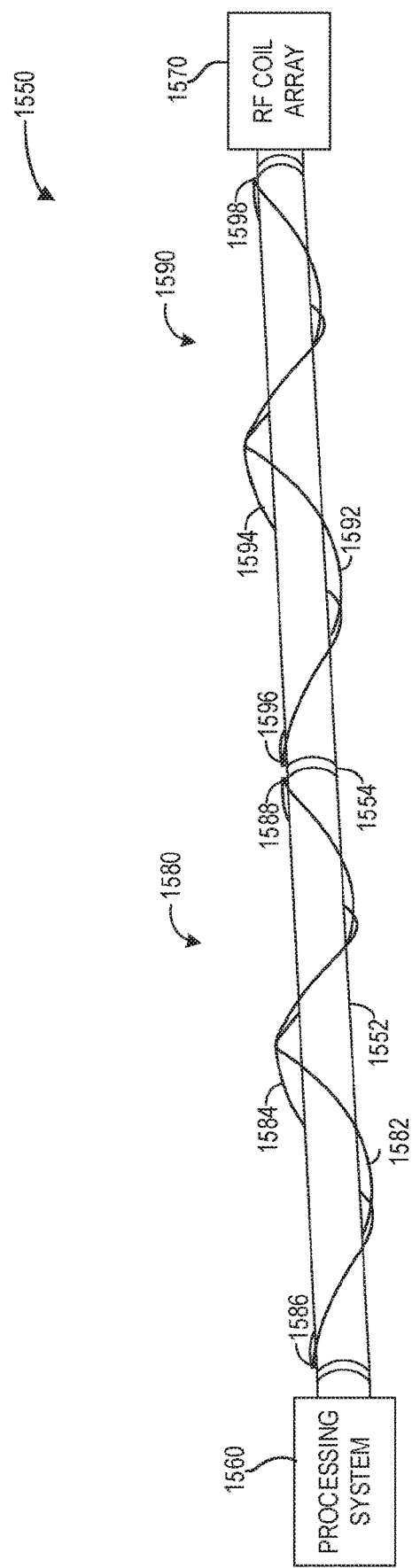

The tapered spiral configuration of the common mode trap conductors described herein above is particularly advantageous when multiple common mode trap conductors are contiguously disposed in a common mode trap assembly. As an illustrative example, FIG. 16 is a perspective view of a RF coil array interfacing cable 1550 including a plurality of continuous and/or contiguous common mode traps coupling an RF coil array 1570 to a processing system 1560. RF coil array interfacing cable 1550 includes a first common mode trap 1580 and a second common mode trap 1590 positioned adjacent to each other on a central conductor 1552.

The first common mode trap 1580 includes a first common mode trap conductor 1582 and a second common mode trap conductor 1584 counterwound in a tapered spiral configuration. To that end, the first and second conductors 1582 and 1584 are fixed to posts 1586 and 1588. It should be noted that the posts 1586 and 1588 are aligned on a same side of the common mode trap 1580.

Similarly, the second common mode trap 1590 includes a third common mode trap conductor 1592 and a fourth common mode trap conductor 1594 counterwound in a tapered spiral configuration and fixed to posts 1596 and 1598. It should be noted that the posts 1596 and 1598 are aligned on a same side of the common mode trap 1590.

As depicted, the common mode traps 1580 and 1590 are separated by a distance, thereby exposing the central conductor 1552 in the gap 1554 between the common mode traps. Due to the tapering spiral configuration of the common mode trap conductors of the common mode traps, the gap 1554 can be minimized or altogether eliminated in order to increase the density of common mode traps in a common mode trap assembly without loss of impedance functions of the common mode traps. That is, the distance can be made arbitrarily small such that the common mode traps are in face-sharing contact, given the tapered spiral configuration.

It should be appreciated that while the RF coil array interfacing cable 1550 includes two common mode traps 1580 and 1590, in practice a RF coil array interfacing cable may include more than two common mode traps.

Further, the common mode traps 1580 and 1590 of the RF coil array interfacing cable 1550 are aligned such that the posts 1586, 1588, 896, and 1598 are aligned on a same side of the RF coil array interfacing cable. However, in examples where cross-talk between the common mode traps may be possible, for example if the tapering of the counterwound conductors is more severe or steep, the common mode traps may be rotated with respect to one another to further reduce fringe effects and/or cross-talk between the traps.

Additionally, other common mode trap or balun configurations are possible. For example, the exterior shielding of each common mode trap may be trimmed such that the common mode traps can be overlapped or interleaved, thus increasing the density of the common mode traps.

The technical effect of a flexible, stretchable RF coil assembly according to the disclosure includes RF coils in an array being positioned more arbitrarily, allowing placement and/or size of the coils to be based on desired anatomy coverage, without having to account for fixed coil overlaps or electronics positioning. Another technical effect is that the coils and coupled stretchable material may conform to the patient anatomy, rigid, or semi-rigid housing contours, allowing the RF coils be positioned in close proximity to the anatomy being imaged, even if the anatomy varies in size and shape. Further, the cost and weight of the coils may be significantly lowered due to minimized materials and production process, and environmentally-friendlier processes may be used in the manufacture and miniaturization of the RF coils of the present disclosure versus conventional coils.

An example provides for a radio frequency (RF) coil assembly for a magnetic resonance imaging (MRI) system. The RF coil assembly includes a loop portion comprising distributed capacitance conductors; a coupling electronics portion including a pre-amplifier; and a stretchable layer of material to which the loop portion and coupling electronics portion are attached. In a first example of the RF coil assembly, the stretchable layer of material comprises one or more of an elastomeric material, a polyester material, cotton, and wool. In a second example of the RF coil assembly, which optionally includes the first example, the stretchable layer of material is in the form of a sleeve adapted to fit over one or more of an arm, a hand, a wrist, an elbow, a leg, a foot, an ankle, and a knee of a subject to be imaged. In a third example of the assembly, which optionally includes one or both of the first and second examples, the stretchable layer of material is in the form of a cylinder adapted to fit over one or more of a neck, a chest, and a torso of a subject to be imaged. In a fourth example of the assembly, which optionally includes one or more or each of the first through third examples, the coupling electronics portion further includes a decoupling circuit and an impedance inverter circuit, the impedance inverter circuit comprising an impedance matching network and an input balun. In a fifth example of the assembly, which optionally includes one or more or each of the first through fourth examples, the pre-amplifier comprises a low input impedance pre-amplifier optimized for high source impedance, and the impedance matching network provides the high source impedance. In a sixth example of the assembly, which optionally includes one or more or each of the first through fifth examples, the distributed capacitance conductors comprise two parallel conductors encapsulated and separated by a dielectric material, a capacitance of the loop portion a function of a spacing between the two parallel conductors, a position and/or number of cuts on the two parallel wires, and the dielectric material. In a seventh example of the assembly, which optionally includes one or more or each of the first through sixth examples, the loop portion is void of any capacitive and inductive lumped components along an entire length of the loop portion between terminating ends thereof. In an eighth example of the assembly, which optionally includes one or more or each of the first through seventh examples, the assembly further includes a coil-interfacing cable extending between the coupling electronics portion and an interfacing connector of the RF coil assembly, the coil-interfacing cable including a first conductor and a second conductor counterwound around a length of a central conductor.

An example provides for a radio frequency (RF) coil array for a magnetic resonance imaging (MRI) system. The RF coil array includes a plurality of RF coils. Each RF coil includes an integrated capacitor coil loop and a coupling electronics unit including a pre-amplifier and impedance matching network configured to generate a high blocking impedance. The RF coil array further includes a stretchable layer of material, and each RF coil is attached to the stretchable layer of material. In a first example of the RF coil array, each RF coil is sewn on the stretchable layer of material. In a second example of the array, which optionally includes the first example, the plurality of RF coils are positioned at non-fixed positions relative to each other. In a third example of the array, which optionally includes one or both of the first and second examples, the array further includes at least one coil-interfacing wire extending from each coupling electronics unit to an interface connector. In a fourth example of the array, which optionally includes one or more or each of the first through third examples, each RF coil is movable in multiple dimensions relative to other RF coils of the RF coil array. In a fifth example of the array, which optionally includes one or more or each of the first through fourth examples, each RF coil is not fixedly coupled to the other RF coils such that each RF coil has an adjustable and variable amount of overlap with the other RF coils of the RF coil array.

An example provides for a radio frequency (RF) coil array for a magnetic resonance imaging (MRI) system. The RF coil array includes a stretchable headwear adapted to fit on a head of a subject to be imaged and a plurality of RF coils coupled to the stretchable headwear. Each RF coil includes an integrated capacitor coil loop and a coupling electronics unit including a pre-amplifier and impedance matching network configured to generate a high blocking impedance. In a first example of the RF coil array, when the stretchable headwear is not worn by the subject, a first RF coil of the plurality of RF coils is separated from a second RF coil of the plurality of RF coils by a first distance, and when the stretchable headwear is worn by the subject, the first RF coil is separated from the second RF coil by a second distance that is longer than the first distance, and a diameter of the first RF coil is the same when the stretchable headwear is not worn by the subject and when the stretchable headwear is worn by the subject. In a second example of the RF coil array that optionally includes the first example, the integrated capacitor coil loop comprises two parallel conductors encapsulated and separated by a dielectric material, the two parallel conductors maintained separate by the dielectric material along an entire length of the loop portion between terminating ends thereof. In a third example of the RF coil array, which optionally includes one or both of the first and second examples, each coupling electronics unit is housed in a common housing. In a fourth example of the RF coil array, which optionally includes one or more or each of the first through third examples, the RF coil array further includes a connector configured to couple one or more coupling electronics units to a coil-interfacing cable.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A radio frequency (RF) coil assembly for a magnetic resonance imaging (MRI) system, comprising:
   a loop portion comprising distributed capacitance conductors;
   a coupling electronics portion including a pre-amplifier;
   a stretchable layer of material to which the loop portion and coupling electronics portion are attached;
   a coil-interfacing cable extending between the coupling electronics portion and an interfacing connector of the RF coil assembly, wherein the coil-interfacing cable comprises a first conductor and a second conductor counterwound around a length of a central conductor;

wherein the counterwound first and second conductors serve as a return path for a current passing through the central conductor;

wherein the coupling electronics portion further includes a decoupling circuit and an impedance inverter circuit, the impedance inverter circuit comprising an impedance matching network and an input balun;

wherein the input balun includes two input terminals and two output terminals; and wherein the one of the two output terminals of the input balun is directly connected to a ground connection and the other output terminal is connected to the impedance matching network.

2. The RF coil assembly of claim 1, wherein the stretchable layer of material comprises one or more of an elastomeric material, a polyester material, cotton, and wool.

3. The RF coil assembly of claim 1, wherein the stretchable layer of material is in the form of a sleeve adapted to fit over one or more of an arm, a hand, a wrist, an elbow, a leg, a foot, an ankle, and a knee of a subject to be imaged.

4. The RF coil assembly of claim 1, wherein the stretchable layer of material is in the form of a cylinder adapted to fit over one or more of a neck, a chest, and a torso of a subject to be imaged.

5. The RF coil assembly of claim 1, wherein the pre-amplifier comprises a low input impedance pre-amplifier optimized for high source impedance, and wherein the impedance matching network provides the high source impedance.

6. The RF coil assembly of claim 1, wherein the distributed capacitance conductors comprise two parallel conductors encapsulated and separated by a dielectric material, the two parallel conductors maintained separate by the dielectric material along an entire length of the loop portion between terminating ends thereof.

7. The RF coil assembly of claim 6, wherein the decoupling circuit includes a decoupling diode which when turned on causes the two parallel conductors to short, wherein the decoupling diode is directly connected to the at least one terminating end.

8. The RF coil assembly of claim 7, wherein each of the two parallel conductors includes a first terminating end and a second terminating end.

9. The RF coil assembly of claim 8, wherein the decoupling diode is directly connected between the two first terminating ends of the two parallel conductors.

10. The RF coil assembly of claim 9, wherein the second terminating end of one of the two parallel conductors is directly connected to one input terminal of the input balun.

11. The RF coil assembly of claim 1, wherein the loop portion is void of any capacitive and inductive lumped components along an entire length of the loop portion between terminating ends thereof.

12. A radio frequency (RF) coil array for a magnetic resonance imaging (MRI) system, comprising:
a plurality of RF coils, each RF coil comprising:
an integrated capacitor coil loop; and
a coupling electronics unit including a pre-amplifier and impedance matching network configured to generate a high blocking impedance;
a stretchable layer of material, each RF coil attached to the stretchable layer of material;
a coil-interfacing cable extending between the coupling electronics unit and an interfacing connector of the RF coil array, wherein the coil-interfacing cable comprises a first conductor and a second conductor counterwound around a length of a central conductor;

wherein the counterwound first and second conductors serve as a return path for a current passing through the central conductor;

wherein the coupling electronics portion further includes a decoupling circuit and an input balun;

wherein the input balun includes two input terminals and two output terminals; and wherein the one of the two output terminals of the input balun is directly connected to a ground connection and the other output terminal is connected to the impedance matching network.

13. The RF coil array of claim 12, wherein each RF coil is sewn on the stretchable layer of material.

14. The RF coil array of claim 12, wherein the plurality of RF coils are positioned at non-fixed positions relative to each other.

15. The RF coil array of claim 12, wherein each RF coil is movable in multiple dimensions relative to other RF coils of the RF coil array.

16. The RF coil array of claim 12, wherein each RF coil is not fixedly coupled to the other RF coils such that each RF coil has an adjustable and variable amount of overlap with the other RF coils of the RF coil array.

17. A radio frequency (RF) coil array for a magnetic resonance imaging (MRI) system, comprising:
a stretchable headwear adapted to fit on a head of a subject to be imaged; and
a plurality of RF coils coupled to the stretchable headwear, each RF coil comprising:
an integrated capacitor coil loop;
a coupling electronics unit including a pre-amplifier and impedance matching network configured to generate a high blocking impedance;
a coil-interfacing cable extending between the coupling electronics unit and an interfacing connector of the RF coil array, wherein the coil-interfacing cable comprises a first conductor and a second conductor counterwound around a length of a central conductor;

wherein the counterwound first and second conductors serve as a return path for a current passing through the central conductor;

wherein the coupling electronics portion further includes a decoupling circuit and an input balun;

wherein the input balun includes two input terminals and two output terminals; and wherein the one of the two output terminals of the input balun is directly connected to a ground connection and the other output terminal is connected to the impedance matching network.

18. The RF coil array of claim 17, wherein when the stretchable headwear is not worn by the subject, a first RF coil of the plurality of RF coils is separated from a second RF coil of the plurality of RF coils by a first distance, and when the stretchable headwear is worn by the subject, the first RF coil is separated from the second RF coil by a second distance that is longer than the first distance, and wherein a diameter of the first RF coil is the same when the stretchable headwear is not worn by the subject and when the stretchable headwear is worn by the subject.

19. The RF coil array of claim 17, wherein the integrated capacitor coil loop comprises two parallel conductors encapsulated and separated by a dielectric material, the two parallel conductors maintained separate by the dielectric material along an entire length of the loop portion between terminating ends thereof.

20. The RF coil array of claim 17, wherein each coupling electronics unit is housed in a common housing.

\* \* \* \* \*